US012778526B2

(12) United States Patent
Horiuchi et al.

(10) Patent No.: US 12,778,526 B2
(45) Date of Patent: Nov. 3, 2026

(54) RADIOGRAPHY UNIT AND RADIOGRAPHY SYSTEM

(71) Applicant: FUJIFILM CORPORATION, Tokyo (JP)

(72) Inventors: Hisatsugu Horiuchi, Kanagawa (JP); Akihito Bettoyashiki, Kanagawa (JP); Tomoaki Nakashima, Kanagawa (JP); Masayoshi Matsuura, Kanagawa (JP); Kyohei Mori, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 120 days.

(21) Appl. No.: 18/939,555

(22) Filed: Nov. 7, 2024

(65) Prior Publication Data

US 2025/0160770 A1 May 22, 2025

(30) Foreign Application Priority Data

Nov. 20, 2023 (JP) ................................. 2023-196967

(51) Int. Cl.
*A61B 6/00* (2006.01)

(52) U.S. Cl.
CPC .......... *A61B 6/4405* (2013.01); *A61B 6/4452* (2013.01)

(58) Field of Classification Search
CPC ............................ A61B 6/4405; A61B 6/4452
See application file for complete search history.

(56) References Cited

U.S. PATENT DOCUMENTS

2019/0160865 A1* 5/2019 Bhat ..................... B60B 19/003
2021/0132633 A1 5/2021 Hoshino
2021/0345977 A1 11/2021 Kumar

FOREIGN PATENT DOCUMENTS

JP 2014-186695 A 10/2014
JP 2021-176505 A 11/2021
WO 2018/216530 A1 11/2018

* cited by examiner

*Primary Examiner* — Hugh Maupin
(74) *Attorney, Agent, or Firm* — SOLARIS Intellectual Property Group, PLLC

(57) ABSTRACT

The radiography unit includes: a wheel portion including a first wheel movable in a first direction by rotation, and a second wheel arranged circumferentially in a rotation direction of the first wheel and movable in a second direction different from the first direction by rotation; a brake mechanism configured to restrict the rotation of the first wheel; and an operation unit configured to receive an operation of changing a state of restriction of the wheel portion by the brake mechanism, the operation being to set a movement direction of the wheel portion to one direction, in which, in a case in which the rotation of the first wheel is restricted by the brake mechanism in response to an operation on the operation unit and movement in another direction intersecting the one direction is restricted, movement in the one direction is enabled by the rotation of the second wheel.

13 Claims, 12 Drawing Sheets

RADIOGRAPHY UNIT AND RADIOGRAPHY SYSTEM

CROSS-REFERENCE TO RELATED APPLICATIONS

The present application claims priority under 35 U.S.C. § 119 to Japanese Patent Application No. 2023-196967, filed on Nov. 20, 2023. The above application is hereby expressly incorporated by reference, in its entirety, into the present application.

BACKGROUND

1. Technical Field

The technology of the present disclosure relates to a radiography unit and a radiography system.

2. Description of the Related Art

JP2014-186695A discloses an autonomous mobile device comprising an object information acquisition unit that acquires detection information of objects present around the autonomous mobile device, a masking unit that masks detection information within a predetermined region from the detection information of the objects acquired by the object information acquisition unit, a local map creation unit that creates a local map of the region around the autonomous mobile device from the detection information masked by the masking unit, a moving unit that moves the autonomous mobile device, a self position estimation unit that estimates a self position based on the local map created by the local map creation unit and the amount of movement of the moving unit, a guiding unit that drives the moving unit based on a user operation to guide the autonomous mobile device, and an environmental map creation unit that creates an environmental map of a movement region from the self position estimated by the self position estimation unit and the local map while being guided by the guiding unit.

JP2021-176505A discloses an omnidirectional mobile device comprising a chassis on which a plurality of wheels that can move in all directions are arranged, a vehicle body arranged on the chassis, a universal joint that connects the chassis and the vehicle body and allows a posture of the vehicle body to be changed relative to the chassis, and a posture stabilization system that moves the chassis in the direction in which the posture of the vehicle body has changed and maintains the posture of the vehicle body stable.

WO2018/216530A discloses a mobile platform. The mobile platform includes a chassis configured to accommodate one or more medical devices, an omnidirectional wheel system including an omnidirectional wheel coupled to the chassis, a battery accommodated in the chassis, the battery being configured to supply power to drive the omnidirectional wheel system and/or supply power to operate the one or more medical devices, and a battery charging system accommodated within the chassis, the battery charging system being configured to facilitate wired and/or wireless charging of the battery.

SUMMARY

In both JP2014-186695A and JP2021-176505A, it is stated that the device can travel in all directions in a case in which omni-wheels rotate by receiving power from a power source, but no consideration is given to the direction in which the device moves in the case of being moved manually. Also, WO2018/216530A discloses a mobile medical device driving platform having a chassis configured to accommodate a medical device and an omnidirectional wheel coupled to the chassis. However, in WO2018/216530A, manual position adjustment of the mobile medical device driving platform during radiography is not taken into consideration. In view of the above, the technology of the present disclosure provides a radiography unit and a radiography system that can facilitate position adjustment in a case in which manual position adjustment is performed.

A first aspect according to the technology of the present disclosure relates to a radiography unit comprising: a wheel portion including a first wheel provided at a lower portion of a unit and movable in a first direction by rotation, and a second wheel arranged circumferentially in a rotation direction of the first wheel and movable in a second direction different from the first direction by rotation; a brake mechanism configured to restrict the rotation of the first wheel; and an operation unit configured to receive an operation of changing a state of restriction of the wheel portion by the brake mechanism, the operation being to set a movement direction of the unit by the wheel portion to one direction, in which, in a case in which the rotation of the first wheel is restricted by the brake mechanism in response to an operation on the operation unit and movement in another direction intersecting the one direction is restricted, movement in the one direction is enabled by the rotation of the second wheel.

A second aspect according to the technology of the present disclosure relates to the radiography unit according to the first aspect, in which a plurality of the wheel portions are provided, and the plurality of wheel portions include a first wheel portion which is the wheel portion disposed in an orientation in which the first direction is the one direction, and a second wheel portion which is the wheel portion disposed in an orientation in which the first direction is the other direction.

A third aspect according to the technology of the present disclosure relates to the radiography unit according to the second aspect, in which the operation unit is configured to receive an operation of setting a movable direction of the radiography unit to either the one direction or the other direction, and in response to the operation on the operation unit, the restriction of the rotation of the first wheel by the brake mechanism in the first wheel portion and the restriction of the rotation of the first wheel by the brake mechanism in the second wheel portion are selectively switched, thereby switching the movable direction to the one direction or the other direction.

A fourth aspect according to the technology of the present disclosure relates to the radiography unit according to the second aspect, in which the number of the first wheel portions and the number of the second wheel portions are the same.

A fifth aspect according to the technology of the present disclosure relates to the radiography unit according to the second aspect, in which the plurality of wheel portions include two or more of the first wheel portions and two or more of the second wheel portions.

A sixth aspect according to the technology of the present disclosure relates to the radiography unit according to the first aspect, in which a plurality of the wheel portions are provided, and the plurality of wheel portions are disposed in such a manner that the first direction is the same.

A seventh aspect according to the technology of the present disclosure relates to the radiography unit according to the sixth aspect, in which the radiography unit is a radiation source unit including a radiation emitting unit configured to emit radiation and an arm that supports the radiation emitting unit, and the arm is configured to move the radiation emitting unit in a direction intersecting a movement direction of the radiography unit.

An eighth aspect according to the technology of the present disclosure relates to the radiography unit according to the first aspect, in which, in the wheel portion, the second direction is a direction orthogonal to the first direction.

A ninth aspect according to the technology of the present disclosure relates to the radiography unit according to the eighth aspect, in which the second wheel is formed of a material having a friction coefficient configured to suppress the movement in the other direction in the wheel portion in which the rotation of the first wheel is restricted by the brake mechanism.

A tenth aspect according to the technology of the present disclosure relates to the radiography unit according to the first aspect, in which, in the wheel portion, the second direction is a direction inclined with respect to the first direction.

An eleventh aspect according to the technology of the present disclosure relates to the radiography unit according to the first aspect, in which the radiography unit is a radiation source unit including a radiation emitting unit configured to emit radiation, and the operation unit is provided in the radiation emitting unit.

A twelfth aspect according to the technology of the present disclosure relates to the radiography unit according to the eleventh aspect, in which the operation unit has a display unit that indicates a movable direction of the radiation source unit, and a display on the display unit is switched depending on an irradiation direction of the radiation by the radiation emitting unit.

A thirteenth aspect according to the technology of the present disclosure relates to a radiography system comprising: a radiation source unit that includes a radiation emitting unit configured to emit radiation; and a detection unit that includes a radiation detection unit configured to detect the radiation, in which the radiation source unit and/or the detection unit is the radiography unit according to the first aspect.

According to the technology of the present disclosure, a radiography unit and a radiography system that can facilitate position adjustment in a case in which manual position adjustment is performed are provided.

DETAILED DESCRIPTION

An example of an embodiment of a radiography system 10 according to the technology of the present disclosure will be described with reference to the accompanying drawings.

In the following description, for convenience of explanation, a front-rear direction (also called a depth direction), a width direction, and a height direction of the radiography system 10 are indicated by three arrows X, Y, and Z. First, the height direction is indicated by an arrow Z, and an arrow Z direction indicated by the arrow Z is defined as an upward direction of the radiography system 10, and an opposite direction thereof is defined as a downward direction. The up-down direction corresponds to the vertical direction. The width direction is indicated by an arrow Y orthogonal to the arrow Z, and a direction indicated by the arrow Y is defined as a forward direction of the radiography system 10, and an opposite direction thereof is defined as a rearward direction. The left-right direction is indicated by an arrow X, which is a direction orthogonal to the arrows Z and Y, and a direction indicated by the arrow X is defined as a left direction of the radiography system 10, and an opposite direction thereof is defined as a right direction. In the following description, the expression using the side, such as an upper side, a lower side, a left side, a right side, a front side, and a rear side, has the same meaning as the expression using the direction.

In the present embodiment, the "vertical direction" refers not only to a perfect vertical direction but also to a vertical direction in the sense of including an error that is generally acceptable in the technical field to which the technology of the present disclosure belongs and that does not contradict the concept of the technology of the present disclosure. The same applies to the "horizontal direction", which refers not only to a perfect horizontal direction but also to a horizontal direction in the sense of including an error that is generally acceptable in the technical field to which the technology of the present disclosure belongs and that does not contradict the concept of the technology of the present disclosure.

First Embodiment

Figure 1:
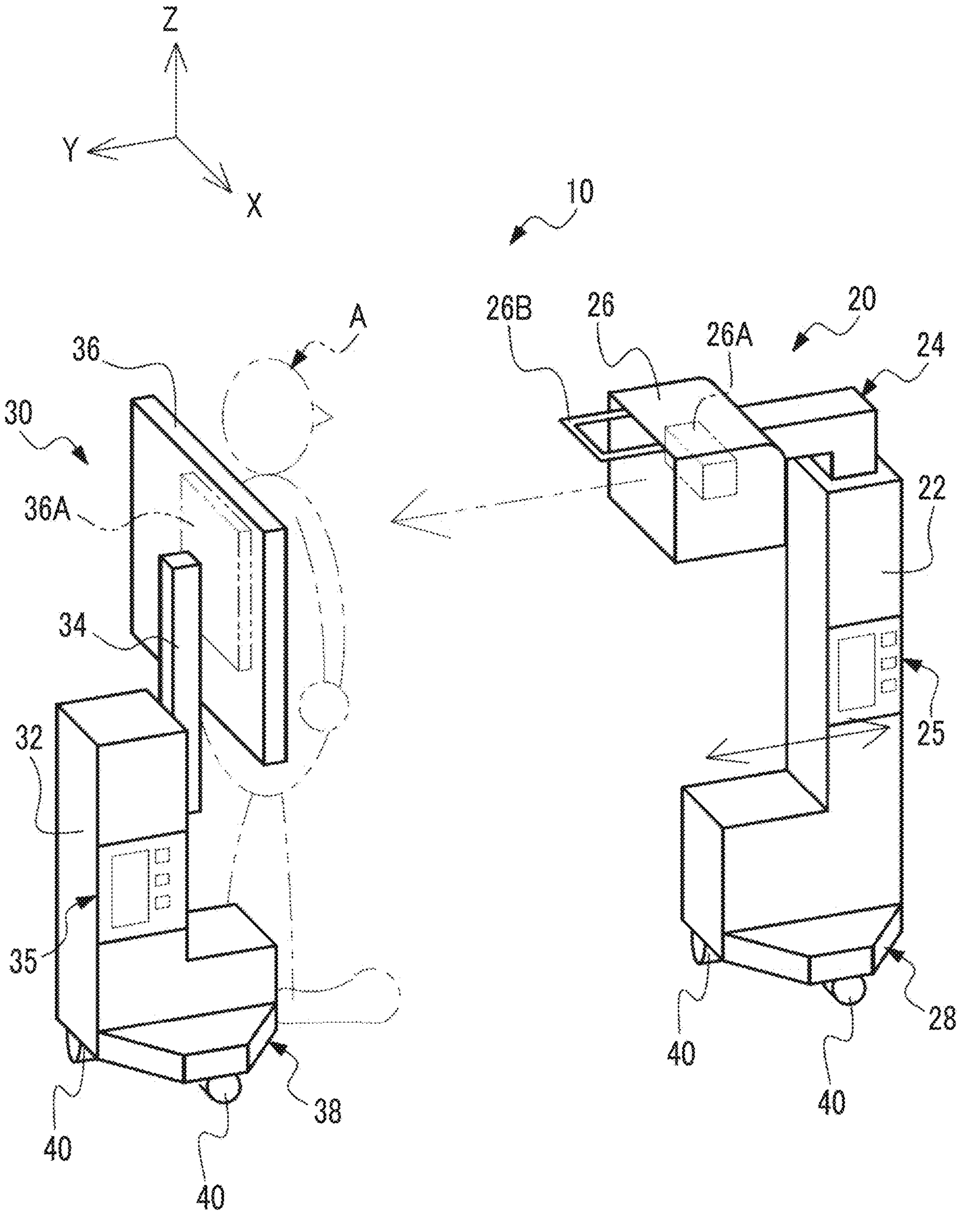
FIG. 1 is a schematic perspective view showing an example of a configuration of a radiography system according to an embodiment.

As an example, as shown in FIG. 1, a radiography system 10 is a system for performing radiography on a subject A. The radiography system 10 includes a radiation source unit 20 and a detection unit 30. The radiation source unit 20 comprises a radiation source 26A and is a device that irradiates the subject A with radiation (for example, X-rays or gamma rays) generated from the radiation source 26A. The detection unit 30 comprises a radiation detector 36A, and is a device that detects radiation that has transmitted through the subject A. In a case in which radiography is performed, the radiation source unit 20 and the detection unit 30 are disposed in positions facing each other. The subject A stands between the radiation source unit 20 and the detection unit 30 and in the vicinity of the detection unit 30. Then, the subject A is irradiated with radiation, and radiography is performed. The radiography system 10 is an example of a "radiography system" according to the technology of the present disclosure, and the radiation source unit 20 and the detection unit 30 are examples of a "radiography unit" according to the technology of the present disclosure. The radiation source unit 20 is an example of a "radiation source unit" according to the technology of the present disclosure, and the detection unit 30 is an example of a "detection unit" according to the technology of the present disclosure.

The radiation source unit 20 comprises a body part 22, an arm 24, and a radiation emitting unit 26. The body part 22 is a part constituting the body portion of the radiation source unit 20, and accommodates therein a power supply system that supplies power to the radiation source 26A, a control device that controls the entire radiation source unit 20, and a mechanism for driving the arm 24, etc.

The arm 24 is a part that extends from the body part 22, with its base end attached to the body part 22 and the radiation emitting unit 26 provided at its tip part. The arm 24 is capable of being displaced in order to move the radiation emitting unit 26 relative to the subject A. Specifically, the arm 24 is expandable and contractible in the up-down direction. The arm 24 is also expandable and contractible in the horizontal direction. This allows the radiation emitting unit 26 to be moved relative to the subject A via the arm 24.

The body part 22 is provided with an operation unit 25. The operation unit 25 is capable of receiving an operation of designating a movement direction of the radiation source unit 20 in a predetermined direction. The operation unit 25 is, for example, an operation panel having buttons capable of designating the movement direction of the radiation source unit 20. The operation unit 25 is provided, for example, on the left side surface of the body part 22. The operation unit 25 is an example of an "operation unit" according to the technology of the present disclosure.

The radiation emitting unit 26 is capable of emitting radiation to the subject A. The radiation emitting unit 26 is attached to the tip part of the arm 24. The radiation emitting unit 26 accommodates a radiation source 26A therein. The irradiation direction of the radiation generated in the radiation source 26A is defined by an irradiation field limiter (not shown) inside the radiation source 26A. Then, the subject A is irradiated with radiation from the radiation source 26A. In the example shown in FIG. 1, the radiation emitting unit 26 emits radiation in the forward direction. The arm 24 is an example of an "arm" according to the technology of the present disclosure, and the radiation emitting unit 26 is an example of a "radiation emitting unit" according to the technology of the present disclosure.

Furthermore, the radiation emitting unit 26 comprises a grip portion 26B. The grip portion 26B is a part that can be gripped by a user of the radiography system 10 (for example, a radiologist or a doctor). A user can move the radiation source unit 20 by holding the grip portion 26B.

In addition, a base portion 28 is provided on the lower side of the body part 22. The base portion 28 is a part that supports the body part 22. In addition, a wheel portion 40 is provided on the lower surface of the base portion 28. The radiation source unit 20 can travel via the wheel portion 40 provided on the body part 22. The radiation source unit 20 can be manually moved by a user (for example, a doctor or a radiologist). Details of the wheel portion 40 will be described later. The wheel portion 40 is an example of a "wheel portion" according to the technology of the present disclosure.

The detection unit 30 comprises a body part 32, an arm 34, and a radiation detection unit 36. The body part 32 is a part constituting the body portion of the detection unit 30, and accommodates therein a power supply system that supplies power to the radiation detector 36A, a control device that controls the entire detection unit 30, and a mechanism for driving the arm 34, etc.

The arm 34 is a part that extends from the body part 32, with its base end attached to the body part 32 and the radiation detection unit 36 provided on its tip end. The arm 34 is capable of being displaced in order to move the radiation detection unit 36 relative to the subject A. Specifically, the arm 34 is a rod-like member provided on the body part 32, and the arm 34 is capable of moving the radiation detection unit 36 in the up-down direction.

The body part 32 is provided with an operation unit 35. The operation unit 35 is capable of receiving an operation of designating a movement direction of the detection unit 30 in a predetermined direction. The operation unit 35 is, for example, an operation panel having buttons capable of designating the movement direction of the detection unit 30. The operation unit 35 is provided, for example, on the left side surface of the body part 32. The operation unit 35 is an example of an "operation unit" according to the technology of the present disclosure.

The radiation detection unit 36 detects the radiation emitted from the radiation emitting unit 26. The radiation detection unit 36 accommodates a radiation detector 36A therein. The radiation detector 36A detects radiation that is emitted from the radiation source 26A and transmits through a diagnosis target part of the subject A, and outputs a radiation image. The radiation detector 36A is called a flat panel detector (FPD). The radiation detector 36A has a scintillator that converts radiation into visible light, and may be an indirect conversion type that converts the visible light emitted by the scintillator into an electric signal, or a direct conversion type that directly converts radiation into an electric signal.

In addition, a base portion 38 is provided on the lower side of the body part 32. The base portion 38 is a part that supports the body part 32. In addition, a wheel portion 40 is provided on the lower surface of the base portion 38. The detection unit 30 can travel via the wheel portion 40 provided on the body part 32. The detection unit 30 can be manually moved by a user (for example, a doctor or a radiologist). Details of the wheel portion 40 will be described later.

Here, in radiography using the radiography system 10, there are cases in which it is necessary to adjust the positional relationship between the radiation source unit 20 and the detection unit 30. For example, by adjusting the distance between the radiation source unit 20 and the detection unit 30, a source to image receptor distance (SID), which is the distance from the focus of the radiation source 26A to the radiation detector 36A, may be adjusted. In this case, it is conceivable that each unit can adjust its position by moving on its own via the wheel portion 40; however, there are limitations on the speed at which the unit can move while traveling and on the minimum distance it can move. Therefore, the time required for position adjustment will be long.

Therefore, the user manually moves the radiation source unit 20 and the detection unit 30 to adjust their positions. In this case, in order to facilitate position adjustment, it is required to move the radiation source unit 20 and the detection unit 30 in only one direction. For example, after determining the position in the left-right direction of the radiation source unit 20 relative to the detection unit 30 (the direction along the X direction shown in FIG. 1), it is necessary to adjust the position in the front-rear direction (the direction along the Y direction shown in FIG. 1). On the other hand, the radiation source unit 20 and the detection unit 30 also need to be able to move freely in various directions to facilitate movement in situations other than position adjustment.

Therefore, the radiation source unit 20 and the detection unit 30 according to the present embodiment are provided with a wheel portion 40. In the following description, the wheel portion 40 provided on the base portion 28 of the radiation source unit 20 will be used as an example, but the wheel portion 40 provided on the base portion 38 of the detection unit 30 has a similar configuration. In the following description, in a case in which there is no need to distinguish between the radiation source unit 20 and the detection unit 30, they may be simply referred to as "each unit".

Figure 2:
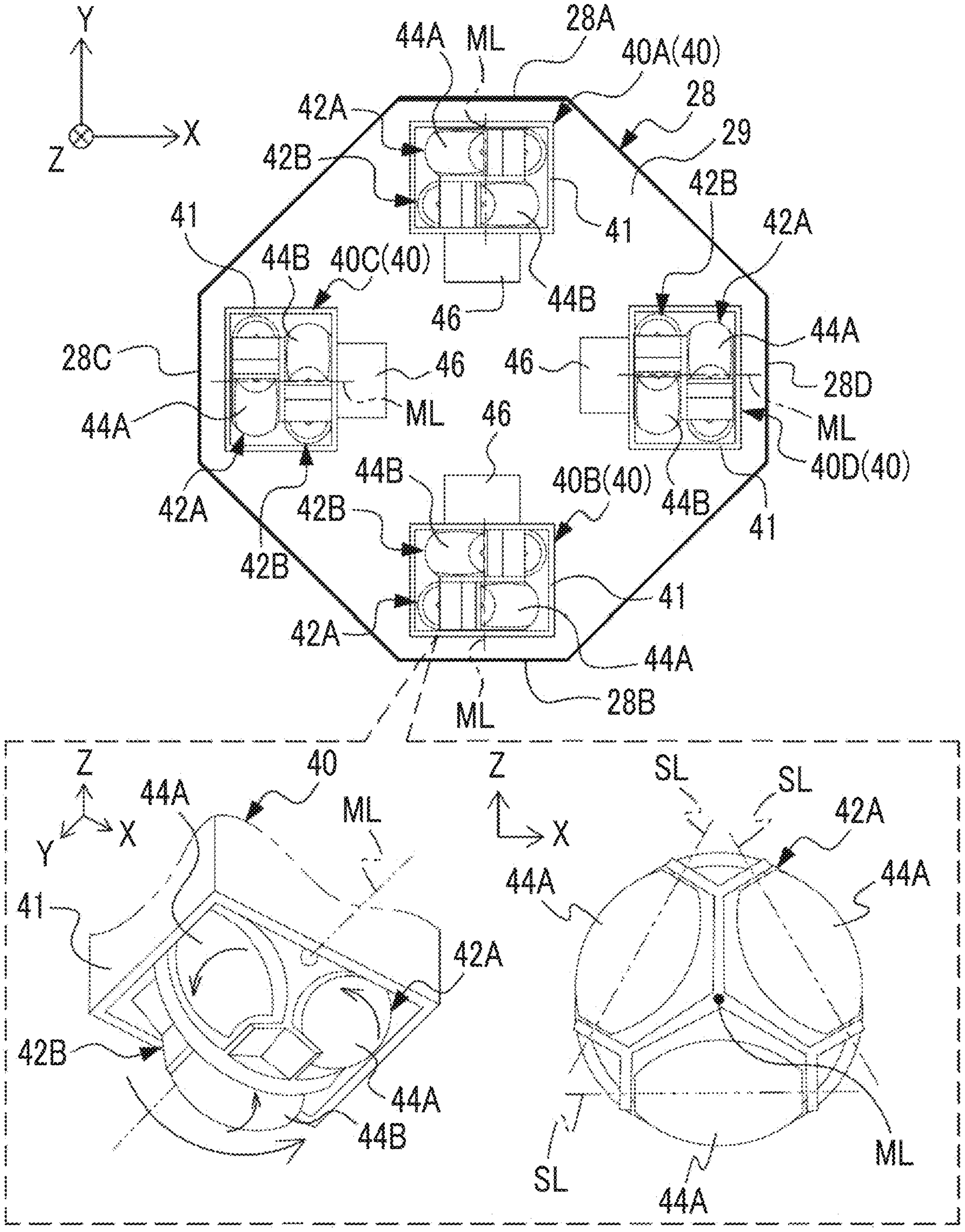
FIG. 2 is a bottom view showing an example of a configuration of a radiation source unit according to the embodiment.

As an example, as shown in FIG. 2, the base portion 28 is provided with a wheel portion 40. Specifically, the wheel portion 40 is attached to the lower surface 29 of the base portion 28. In the example shown in FIG. 2, a plurality of wheel portions 40 are provided. The wheel portions 40 are provided at both end portions of the base portion 28 in the front-rear direction one by one, and further at both end portions of the base portion 28 in the left-right direction one by one.

Specifically, in the example shown in FIG. 2, four wheel portions 40A to 40D are provided. The base portion 28 has an octagonal outer frame as viewed from below, with a wheel portion 40A provided at a position corresponding to a front side 28A of the octagon, and a wheel portion 40B provided at a position corresponding to a rear side 28B. In addition, a wheel portion 40C is provided at a position corresponding to a right side 28C of the octagon, and a wheel portion 40D is provided at a position corresponding to a left side 28D. Hereinafter, in a case in which there is no need to distinguish between the wheel portions 40A to 40D, they will be simply referred to as a "wheel portion 40".

The wheel portion 40 has main wheels 42A and 42B. The main wheels 42A and 42B are wheels for enabling the radiation source unit 20 to travel. The main wheels 42A and 42B have approximately the same outer diameter. In addition, the main wheels 42A and 42B are rotatable about a common rotation axis ML. Except in the case of manual position adjustment, the main wheels 42A and 42B may be rotatable by receiving power from a power source not shown, and the main wheels 42A and 42B rotate simultaneously by receiving power from a power source not shown. In other words, the main wheels 42A and 42B passively rotate in the case of manual position adjustment by the user. The main wheels 42A and 42B are disposed adjacent to each other along the direction of the rotation axis ML. The upper portions of the main wheels 42A and 42B are accommodated in a housing 41. The main wheels 42A and 42B are examples of a "first wheel" according to the technology of the present disclosure.

The wheel portion 40 has auxiliary wheels 44A arranged circumferentially in the rotation direction of the main wheels 42A. Specifically, the main wheel 42A includes auxiliary wheels 44A, and the auxiliary wheels 44A are attached along the outer periphery of the main wheels 42A. In other words, the auxiliary wheels 44A form the outer peripheral surface of the main wheels 42A that can come into contact with the ground. The auxiliary wheel 44A has a spindle shape and is rotatable about a rotation axis SL that is aligned with the central axis of the spindle shape. The rotation axis SL of the auxiliary wheel 44A is orthogonal to the rotation axis ML of the main wheel 42A. In other words, the direction of movement caused by the rotation of the auxiliary wheels 44A is orthogonal to the direction of movement caused by the rotation of the main wheels 42A. Additionally, the auxiliary wheels 74 rotate passively in the case of manual position adjustment. In the example shown in FIG. 2, three auxiliary wheels 44A are provided, and are disposed at 120° intervals in the circumferential direction of the main wheels 42A. The auxiliary wheel 44A is an example of a "second wheel" according to the technology of the present disclosure.

The auxiliary wheels 44A are formed of a material having a friction coefficient capable of suppressing movement due to rotation of the main wheels 42A in a state in which the rotation of the main wheels 42A is restricted by a brake mechanism 46. The auxiliary wheels 44A are formed of, for example, a synthetic resin material (for example, rubber).

The main wheel 42B is also provided with an auxiliary wheel 44B, similarly to the auxiliary wheel 44A of the main wheel 42A. However, the circumferential disposition of the auxiliary wheels 44B on the main wheels 42B is shifted by 60° with respect to the rotation axis ML with respect to the circumferential disposition of the auxiliary wheels 44A on the main wheels 42A. Accordingly, in a region of the main wheel 42A where there is no ground contact surface (that is, a region where the auxiliary wheel 44A is not provided), the auxiliary wheel 44B of the main wheel 42B is adapted to come into contact with the ground. As a result, either the main wheel 42A or the main wheel 42B of the wheel portion 40 comes into contact with the ground, thereby achieving stable movement by the wheel portion 40.

The main wheels 42A and 42B are, for example, so-called Omni-Wheels (registered trademark). Although an omni-wheel having three auxiliary wheels 44A and 44B is given as an example here, this is merely one example. For example, there may be three or more auxiliary wheels 44A and 44B. In addition, an example of a form in which a pair of main wheels 42A and 42B are provided on one wheel portion 40 has been described, but this is merely one example, and one main wheel may be provided on one wheel portion 40. In this case, by increasing the number of auxiliary wheels provided on the main wheels (for example, 30 wheels) and increasing the surface area in contact with the ground, movement due to rotation of the main wheels can be stabilized.

In the wheel portions 40A and 40B, the rotation axes ML of the pair of main wheels 42A and 42B are oriented in the same direction. In other words, in the wheel portions 40A and 40B, the directions of movement caused by the rotation of the pair of main wheels 42A and 42B are the same. Here, in the wheel portions 40A and 40B, the rotation axis ML is along the front-rear direction (the direction along the Y direction shown in FIG. 2), and the direction in which they can move is the left-right direction (the direction along the X direction shown in FIG. 2). The wheel portions 40A and 40B are examples of a "first wheel portion" according to the technology of the present disclosure.

On the other hand, in the wheel portions 40C and 40D, the rotation axes ML of the pair of main wheels 42A and 42B are also oriented in the same direction. In other words, in the wheel portions 40C and 40D, the directions of movement caused by the rotation of the pair of main wheels 42A and 42B are the same. Here, in the wheel portions 40C and 40D, the rotation axis ML is along the left-right direction (the direction along the X direction shown in FIG. 2), and the direction in which they can move is the front-rear direction (the direction along the Y direction shown in FIG. 2). The wheel portions 40C and 40D are examples of a "second wheel portion" according to the technology of the present disclosure.

Thus, the plurality of wheel portions 40 include wheel portions 40A and 40B whose movable direction due to rotation of the main wheels 42A and 42B is the left-right direction. The plurality of wheel portions 40 also include wheel portions 40C and 40D whose movable direction due to rotation of the main wheels 42A and 42B is the front-rear direction orthogonal to the left-right direction. In addition, the number of wheel portions 40 whose movable direction due to the rotation of the main wheels 42A and 42B is the left-right direction is the same as the number of wheel portions 40 whose movable direction due to the rotation of the main wheels 42A and 42B is the front-rear direction. In a state of not being braked by the brake mechanism 46, the radiation source unit 20 is movable in the front-rear direction and the left-right direction by the plurality of wheel portions 40.

The brake mechanism 46 is provided on the base portion 28. The brake mechanism 46 is a mechanism capable of restricting the rotation of the main wheels 42A and 42B of the wheel portion 40. The brake mechanism 46 is not particularly limited, and a general wheel braking mechanism may be employed. In the example shown in FIG. 2, the brake mechanism 46 is provided for each of the plurality of wheel portions 40. The brake mechanism 46 is an example of a "brake mechanism" according to the technology of the present disclosure.

Figure 3:
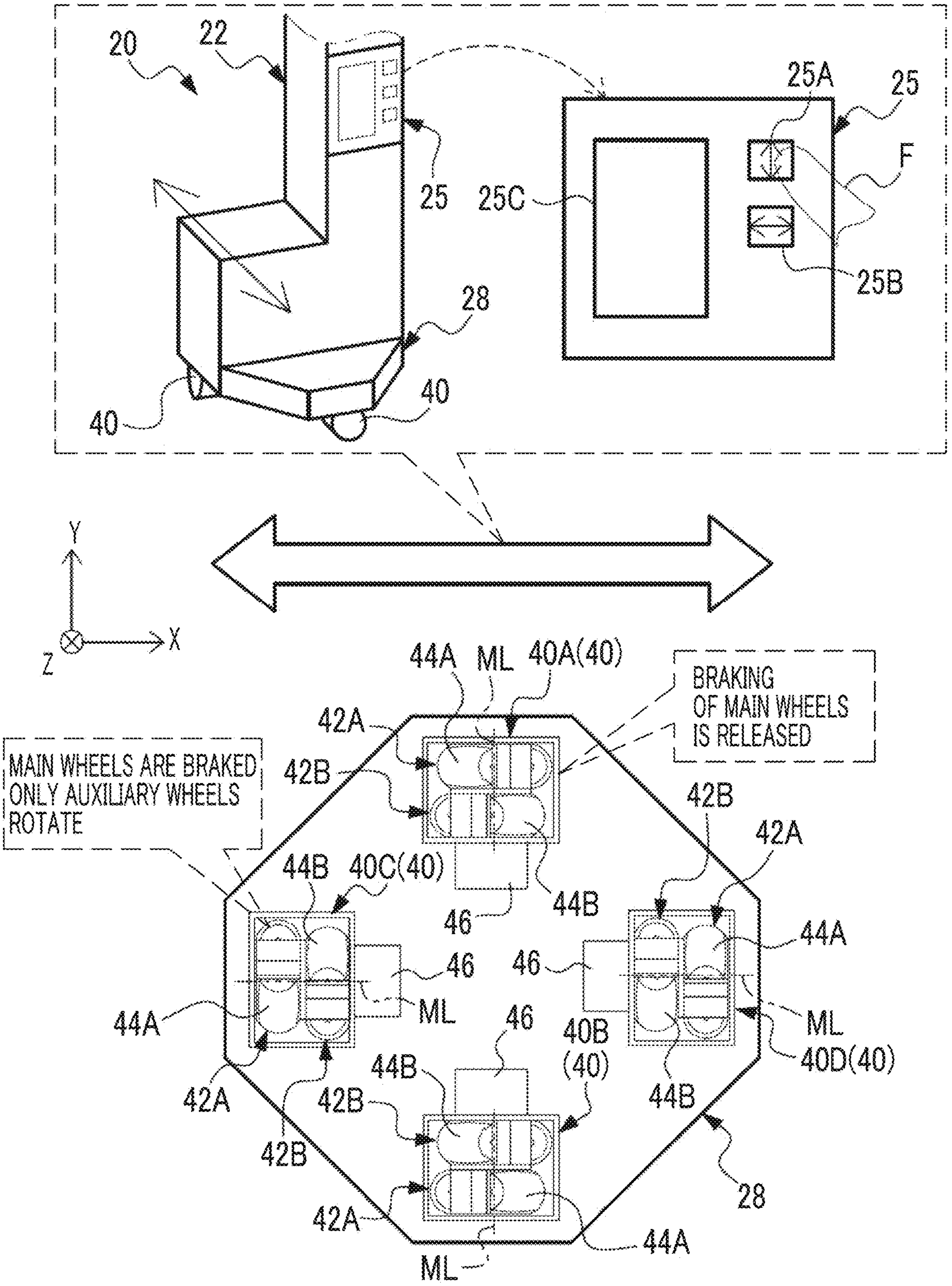
FIG. 3 is a conceptual diagram showing an example of a configuration of the radiation source unit according to the embodiment.

As described above, in the case of adjusting the position of the radiation source unit 20, first, the rough position of the radiation source unit 20 is set. Then, the brake mechanism 46 of the radiation source unit 20 is actuated to restrict the movement of the radiation source unit 20. From this state, the user manually moves the radiation source unit 20 only in a predetermined direction to adjust the position. Therefore, as an example, as shown in FIG. 3, the operation unit 25 is capable of receiving an operation of setting the direction of movement of the radiation source unit 20 by the wheel portion 40 to a predetermined direction. Specifically, the operation unit 25 can receive an operation of setting the movable direction of the radiation source unit 20 to either the left-right direction or the front-rear direction.

In the example shown in FIG. 3, a left/right movement button 25A provided on the operation unit 25 is pressed by the user's finger F. Accordingly, an operation of setting the movement direction of the radiation source unit 20 to the left-right direction (the direction along the X direction shown in FIG. 3) is received.

Note that, although an example of a form in which the left/right movement button 25A is pressed on the operation unit 25 has been described here, the technology of the present disclosure is not limited thereto. For example, in a case in which the operation unit 25 is a touch panel, the left/right movement button 25A may be a soft button displayed on the screen.

The operation unit 25 may include a display 25C capable of displaying information relating to the position of the radiation source unit 20. On the display 25C, the SID is displayed or the angle of the radiation source unit 20 with respect to the detection unit 30 is displayed.

In response to an operation on the operation unit 25, the brake mechanism 46 restricts the rotation of the main wheels 42A and 42B. Here, since an operation of setting the movement direction of the radiation source unit 20 to the left-right direction has been received, the brake mechanism 46 restricts the movement of the wheel portion 40 in the front-rear direction. Specifically, the rotation of the main wheels 42A and 42B in the wheel portion 40C and the wheel portion 40D is restricted by the brake mechanism 46. On the other hand, in the wheel portions 40A and 40B in which the direction of movement caused by the rotation of the main wheels 42A and 42B is the left-right direction, the restriction by the brake mechanism 46 is released.

After the state of restriction of the wheel portion 40 by the brake mechanism 46 is changed in response to an operation on the operation unit 25, the radiation source unit 20 is manually moved by the user. In the example shown in FIG. 3, the radiation source unit 20 is moved in the left-right direction by rotation of the main wheels 42A and 42B of the wheel portions 40A and 40B, respectively. In addition, in the wheel portions 40C and 40D, the rotation of the main wheels 42A and 42B is restricted by the brake mechanism 46.

Here, in the wheel portions 40C and 40D, the rotation of the auxiliary wheels 44A and 44B is not restricted. Furthermore, the direction of movement caused by the rotation of the auxiliary wheels 44A and 44B of the wheel portions 40C and 40D is the left-right direction. Therefore, the radiation source unit 20 can move in the left-right direction not only by the rotation of the main wheels 42A and 42B of the wheel portions 40A and 40B, but also by the rotation of the auxiliary wheels 44A and 44B of the wheel portions 40C and 40D.

Further, the auxiliary wheels 44A and 44B are formed of a material having a friction coefficient capable of restricting movement in the front-rear direction. That is, in the wheel portions 40C and 40D, the movement in the front-rear direction is also restricted by the contact of the auxiliary wheels 44A and 44B with the floor surface.

In this manner, in the wheel portions 40C and 40D in which the rotation of the main wheels 42A and 42B is restricted, movement in the left-right direction is achieved by the rotation of the auxiliary wheels 44A and 44B. The user adjusts the position of the radiation source unit 20 in the left-right direction.

Figure 4:
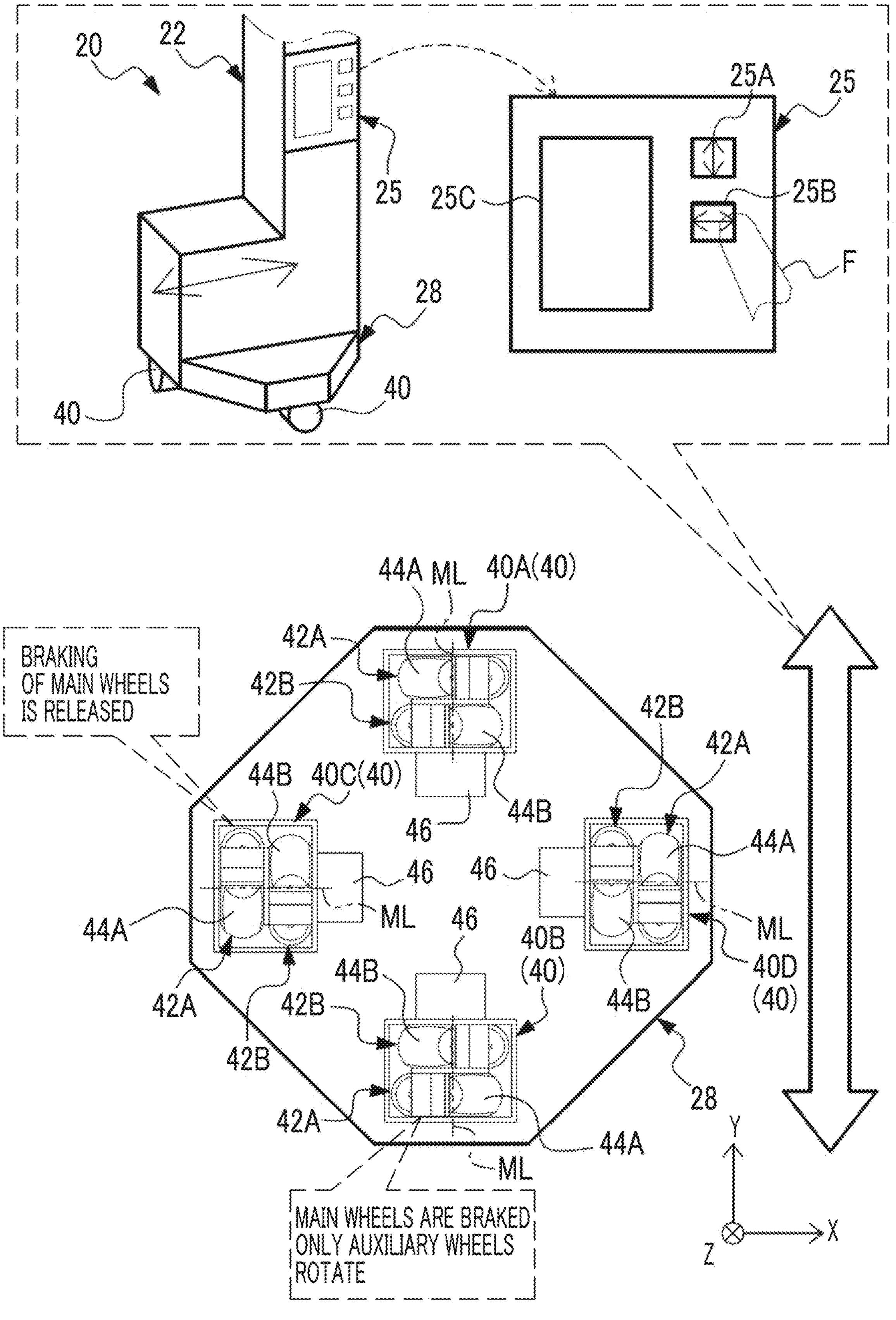
FIG. 4 is a conceptual diagram showing an example of a configuration of the radiation source unit according to the embodiment.

Next, the user adjusts the position of the radiation source unit 20 in the front-rear direction. As an example, as shown in FIG. 4, a forward/backward movement button 25B provided on the operation unit 25 is pressed by the user's finger F. Accordingly, an operation of setting the movement direction of the radiation source unit 20 to the front-rear direction (the direction along the Y direction shown in FIG. 3) is received.

Since an operation of setting the movement direction of the radiation source unit 20 to the front-rear direction has been received, the brake mechanism 46 restricts the movement of the wheel portion 40 in the left-right direction. Specifically, the rotation of the main wheels 42A and 42B in the wheel portion 40A and the wheel portion 40B is restricted by the brake mechanism 46. On the other hand, in the wheel portions 40C and 40D in which the direction of movement caused by the rotation of the main wheels 42A and 42B is the left-right direction, the restriction by the brake mechanism 46 is released.

After the state of restriction of the wheel portion 40 by the brake mechanism 46 is changed in response to an operation on the operation unit 25, the radiation source unit 20 is manually moved by the user. In the example shown in FIG. 4, the radiation source unit 20 is moved in the front-rear direction by rotation of the main wheels 42A and 42B of the wheel portions 40C and 40D, respectively. In addition, in the wheel portions 40A and 40B, the rotation of the main wheels 42A and 42B is restricted by the brake mechanism 46.

Here, in the wheel portions 40A and 40B, the rotation of the auxiliary wheels 44A and 44B is not restricted. Furthermore, the direction of movement caused by the rotation of the auxiliary wheels 44A and 44B of the wheel portions 40A and 40B is the front-rear direction. Therefore, the radiation source unit 20 can move in the front-rear direction not only by the rotation of the main wheels 42A and 42B of the wheel portions 40C and 40D, but also by the rotation of the auxiliary wheels 44A and 44B of the wheel portions 40C and 40D.

Further, the auxiliary wheels 44A and 44B are formed of a material having a friction coefficient capable of restricting movement in the left-right direction. That is, in the wheel portions 40A and 40B, the movement in the left-right direction is also restricted by the contact of the auxiliary wheels 44A and 44B with the floor surface.

In this manner, in the wheel portions 40A and 40B in which the rotation of the main wheels 42A and 42B is restricted, movement in the front-rear direction is achieved by the rotation of the auxiliary wheels 44A and 44B. The user adjusts the position of the radiation source unit 20 in the front-rear direction.

In this way, in response to an operation on the operation unit 25, the restriction of the rotation of the main wheels 42A and 42B by the brake mechanisms 46 in the wheel portions 40A and 40B and the restriction of the rotation of the main wheels 42A and 42B by the brake mechanisms 46 in the wheel portions 40C and 40D are selectively switched. Accordingly, the movable direction of the radiation source unit 20 is switched between the left-right direction and the front-rear direction.

Although the above description has been given of manual position adjustment of the radiation source unit 20 by the user, it goes without saying that the position of the detection unit 30 may also be adjusted in a similar manner. Also, an example has been described in which the position adjustment in the left-right direction is followed by the position adjustment in the front-rear direction, but the order may be reversed, and the position adjustment may be performed a plurality of times. Also, only one of the position adjustments in the left-right direction and the front-rear direction may be performed. Further, manual position adjustment includes a completely manual adjustment performed only by the user's operation, and also includes a manual position adjustment performed in a state in which the wheel portion 40 is assisted by a driving force from a driving source.

As described above, in the radiation source unit 20 according to the present embodiment, the wheel portion 40 is provided on the base portion 28. The wheel portion 40 has main wheels 42A and 42B. The wheel portion 40 also comprises auxiliary wheels 44A and 44B disposed circumferentially in the rotation direction of the main wheels 42A and 42B. The direction of movement caused by the rotation of the auxiliary wheels 44A and 44B is orthogonal to the direction of movement caused by the rotation of the main wheels 42A and 42B. In addition, a brake mechanism 46 capable of restricting the rotation of the main wheels 42A and 42B is provided on the base portion 28 of the radiation source unit 20. Furthermore, an operation unit 25 is provided on the body part 22 of the radiation source unit 20. The operation unit 25 is capable of receiving an operation of setting the direction of movement of the wheel portion 40 to a predetermined direction.

In the radiography system 10, the positions of the units may be adjusted manually. In this case, by making each unit movable only in one direction and not movable in the other direction, manual position adjustment becomes easier. For example, there may be a case in which only the distance of the radiation source unit 20 to the detection unit 30 is adjusted. In this configuration, in a case in which the rotation of the main wheels 42A and 42B of the wheel portions 40A and 40B is restricted by the brake mechanism 46 in response to an operation on the operation unit 25, for example, movement in the left-right direction is restricted. In this case, movement in the front-rear direction is possible by rotation of the main wheels 42A and 42B of the wheel portions 40C and 40D. In addition, movement in the front-rear direction is possible by rotation of the auxiliary wheels 44A and 44B of the wheel portions 40A and 40B. Accordingly, the movable direction of the radiation source unit 20 is limited to only one direction (only the front-rear direction in this case), making it easy to manually adjust the position of the radiation source unit 20.

Further, the radiation source unit 20 according to the present embodiment is provided with a plurality of wheel portions 40A to 40D. The wheel portions 40A and 40B are disposed in an orientation in which the direction of movement caused by the rotation of the main wheels 42A and 42B is the left-right direction. Further, the wheel portions 40C and 40D are disposed in an orientation in which the direction of movement caused by the rotation of the main wheels 42A and 42B is the front-rear direction. Accordingly, it is achieved that the radiation source unit 20 moves stably in the left-right direction and the front-rear direction. For example, compared to a case in which all the wheel portions 40 are attached in the same orientation, movement is achieved by rotation of the main wheels 42A and 42B in both the left-right direction and the front-rear direction. This stabilizes the movement of the radiation source unit 20 in both directions.

In addition, in the radiation source unit 20 according to the present embodiment, the operation unit 25 is capable of receiving an operation of setting the movable direction of the radiation source unit 20 to the front-rear direction or the left-right direction. Then, in response to an operation on the operation unit 25, the restriction of the rotation of the main wheels 42A and 42B by the brake mechanisms 46 in the wheel portions 40A and 40B and the restriction of the rotation of the main wheels 42A and 42B by the brake mechanisms 46 in the wheel portions 40C and 40D are selectively switched. This makes it possible to easily switch the movable direction of the radiation source unit 20 by operating the operation unit 25.

Further, the radiation source unit 20 according to the present embodiment is provided with two wheel portions 40A and 40B, and two wheel portions 40C and 40D. In other words, the number of wheel portions 40 whose movement due to the rotation direction of the main wheels 42A and 42B is in the front-rear direction and the number of wheel portions 40 whose movement due to rotation of the main wheels 42A and 42B is in the left-right direction are the same. Accordingly, the rolling resistance in each of the two movement directions is approximately the same, and thus the force required for manual movement is approximately the same, making position adjustment easier.

Further, the radiation source unit 20 according to the present embodiment is provided with wheel portions 40A and 40B, and wheel portions 40C and 40D. Accordingly, stable movement is possible in each of the two movement directions (here, the front-rear direction and the left-right direction) using the two wheel portions 40. For example, in a case in which movement is possible only in one of two movement directions (for example, the front-rear direction) using only one wheel portion 40, there is a concern that movement will become unstable in that direction. In this configuration, the radiation source unit 20 can be moved while being supported by the two wheel portions 40 in each of the two movement directions, making it easy to manually adjust the position.

In addition, in the radiation source unit 20 according to the present embodiment, the direction of movement caused by the rotation of the auxiliary wheels 44A and 44B is orthogonal to the direction of movement caused by the rotation of the main wheels 42A and 42B. Accordingly, because the main wheels 42A and 42B of the wheel portion 40 arc omni-wheels, it is possible to achieve stable manual movement in two orthogonal directions (for example, the left-right direction and the front-rear direction).

Furthermore, in the radiation source unit 20 according to the present embodiment, the auxiliary wheels 44A and 44B are formed of a material having a friction coefficient capable of restricting movement in the direction of movement caused by the rotation of the main wheels 42A and 42B in the wheel portion 40 in which the rotation of the main wheels 42A and 42B is restricted by the brake mechanism 46. Accordingly, restriction on movement in a direction unintended by the user during manual movement is achieved not only by braking using the brake mechanism 46 but also by the frictional force between the auxiliary wheels 44A and 44B and the floor surface.

In the above first embodiment, an example of a form in which the operation unit 25 is an operation panel has been shown, but the technology of the present disclosure is not limited thereto. For example, the operation unit 25 may be a brake release lever provided on a handle for moving each unit. In this case, a lever for releasing the restriction on movement in the front-rear direction and a lever for releasing the restriction on movement in the left-right direction are provided. By operating these release levers, the movable direction of the radiation source unit can be selectively switched.

First Modification Example

In the above first embodiment, an example of a form in which the four wheel portions 40A to 40D are provided has been described, but the technology of the present disclosure is not limited thereto. The number and disposition of the wheel portions 40 are not particularly limited. As an example, as shown in <A> of FIG. 5, two wheel portions 40 and a ball caster 50 may be provided on the base portion 28. In this case, the two wheel portions 40 are disposed in such a manner that the rotation axes of the main wheels 42A and 42B are orthogonal to each other. In addition, the two wheel portions 40 and the ball caster 50 are disposed at positions of the vertices of an imaginary triangle formed within the frame of the base portion 28 in a case in which the base portion 28 is viewed from below.

Figure 5:
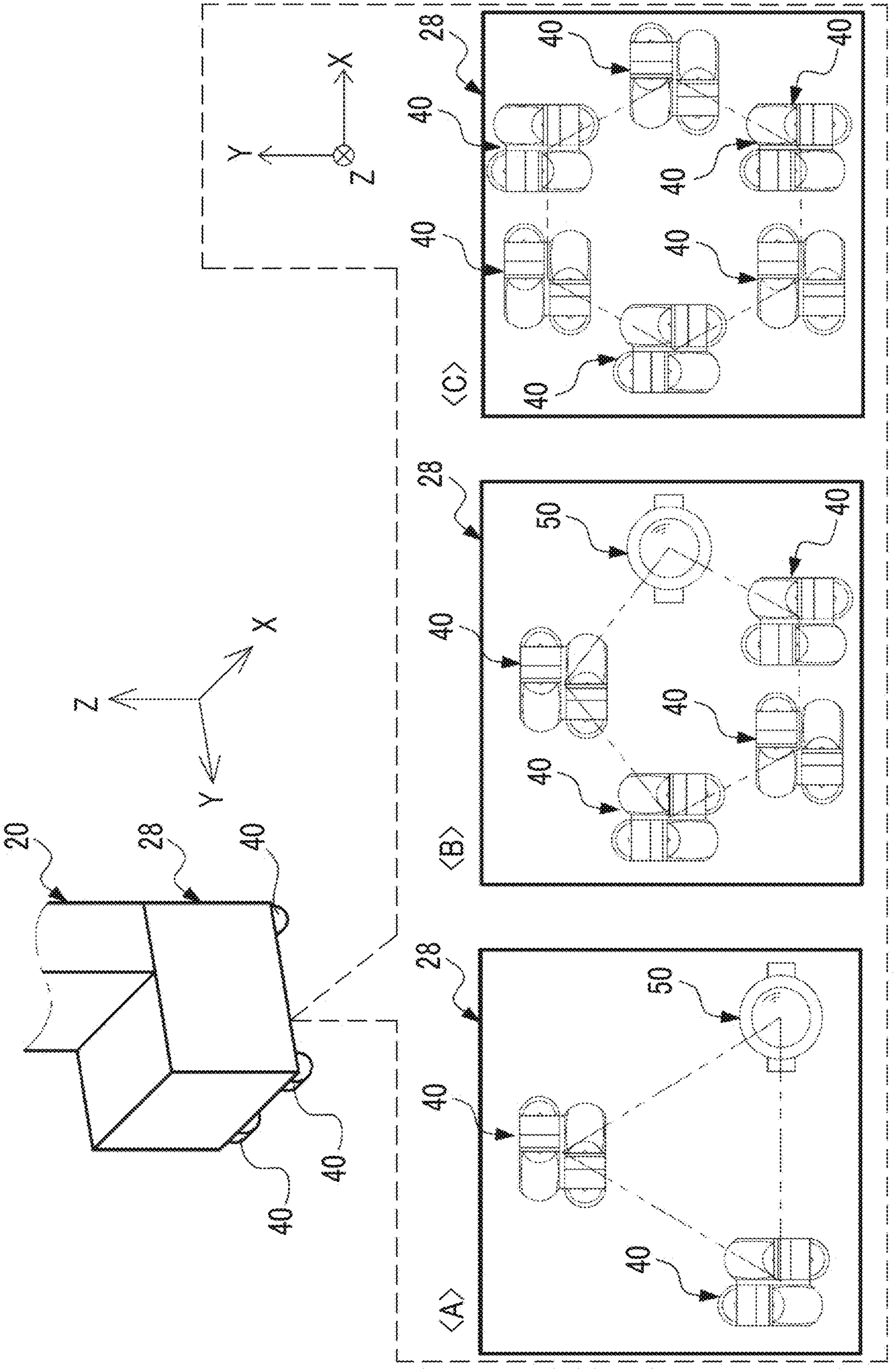
FIG. 5 is a conceptual diagram showing an example of a configuration of the radiation source unit according to the embodiment.

Also, as shown in <B> of FIG. 5 as an example, the four wheel portions 40 and the ball caster 50 may be provided on the base portion 28. The four wheel portions 40 and the ball caster 50 are disposed at positions of the vertices of an imaginary pentagon formed within the frame of the base portion 28 in a case in which the base portion 28 is viewed from below. In this case, each of the four wheel portions 40 is disposed in such a manner that the rotation axes of the main wheels 42A and 42B of the wheel portions 40 positioned at adjacent vertices are orthogonal to each other.

Also, as shown in <C> of FIG. 5 as an example, the six wheel portions 40 may be provided on the base portion 28. The six wheel portions 40 are disposed at positions of the vertices of an imaginary hexagon formed within the frame of the base portion 28 in a case in which the base portion 28 is viewed from below. In this case, each of the six wheel portions 40 is disposed in such a manner that the rotation axes of the main wheels 42A and 42B of the wheel portions 40 positioned at adjacent vertices are orthogonal to each other.

In addition, in the present modification example, an example of a form in which the ball caster 50 is used has been described, but the technology of the present disclosure is not limited thereto. Any wheels that do not restrict the direction of movement may be used, and casters, for example, may be used.

Second Embodiment

In the above first embodiment, an example of a form in which the wheel portions 40A and 40B and the wheel portions 40C and 40D are disposed in such a manner that the rotation axes ML are orthogonal to each other has been described, but the technology of the present disclosure is not limited thereto. In a second embodiment, the wheel portions 40A to 40D are disposed in such a manner that the directions of movement caused by rotation of the main wheels 42A and 42B are in the same orientation.

Figure 6:
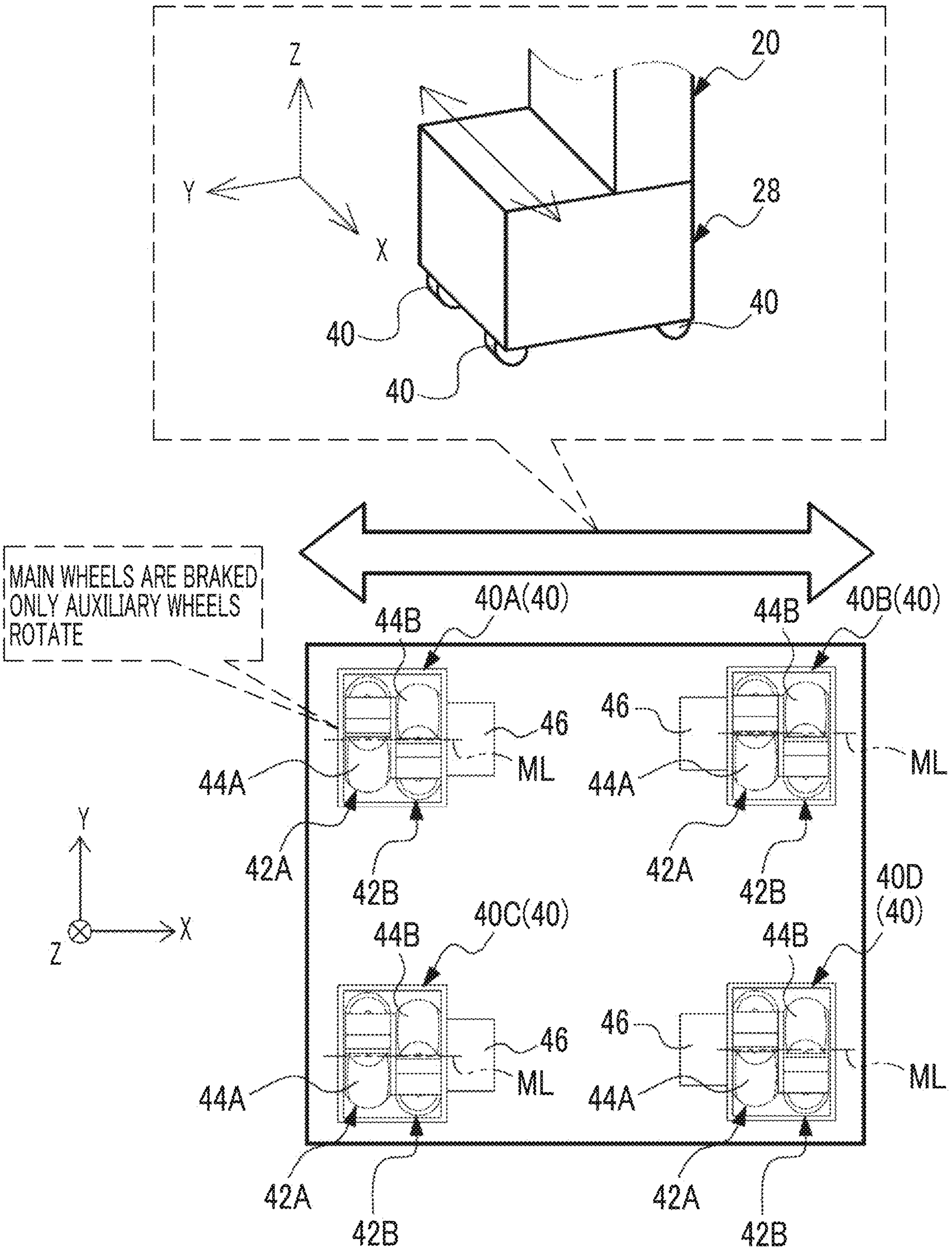
FIG. 6 is a conceptual diagram showing an example of a configuration of the radiation source unit according to the embodiment.

As an example, as shown in FIG. 6, the base portion 28 is provided with a plurality of wheel portions 40. In the example shown in FIG. 6, the base portion 28 has a quadrangular outer frame, and the four wheel portions 40A to 40D are provided at the four corners of the outer frame of the base portion 28. The directions of movement caused by rotation of the main wheels 42A and 42B of the four wheel portions 40A to 40D are in the same orientation. In the example shown in FIG. 6, the directions of movement caused by the rotation of the main wheels 42A and 42B of the four wheel portions 40A to 40D are all aligned in the front-rear direction (the direction along the Y direction shown in FIG. 6). In other words, in the wheel portions 40A to 40D, the rotation axes ML of the main wheels 42A and 42B are all aligned in the left-right direction (the direction along the X direction shown in FIG. 6).

In a case in which the position of the radiation source unit 20 is adjusted, first, the operation unit 25 is operated, and the brake mechanism 46 restricts the movement of the wheel portions 40A to 40D. Then, after the state of restriction of the wheel portion 40 by the brake mechanism 46 is changed in response to an operation on the operation unit 25, the radiation source unit 20 is manually moved by the user. That is, the rotation of the main wheels 42A and 42B of the wheel portions 40A to 40D is restricted by the brake mechanism 46. This restricts the movement of the wheel portions 40A to 40D in the front-rear direction.

Here, in the wheel portions 40A to 40D, the rotation of the auxiliary wheels 44A and 44B is not restricted. Furthermore, the direction of movement caused by the rotation of the auxiliary wheels 44A and 44B of the wheel portions 40A to 40D is the left-right direction. Therefore, the radiation source unit 20 can move in the left-right direction by rotating the auxiliary wheels 44A and 44B of the wheel portions 40A to 40D. In this manner, in the wheel portions 40A to 40D in which the rotation of the main wheels 42A and 42B is restricted by the brake mechanism 46, movement in the left-right direction is possible by the rotation of the auxiliary wheels 44A and 44B. The user manually adjusts the position of the radiation source unit 20 in the left-right direction.

Note that, here, an example has been described in which the directions of movement caused by the rotation of the main wheels 42A and 42B of the four wheel portions 40A to 40D are all aligned in the front-rear direction (the direction along the Y direction shown in FIG. 6), but this is merely one example. It goes without saying that the directions of movement caused by the rotation of the main wheels 42A and 42B of the four wheel portions 40A to 40D may all be aligned in the left-right direction.

Figure 7:
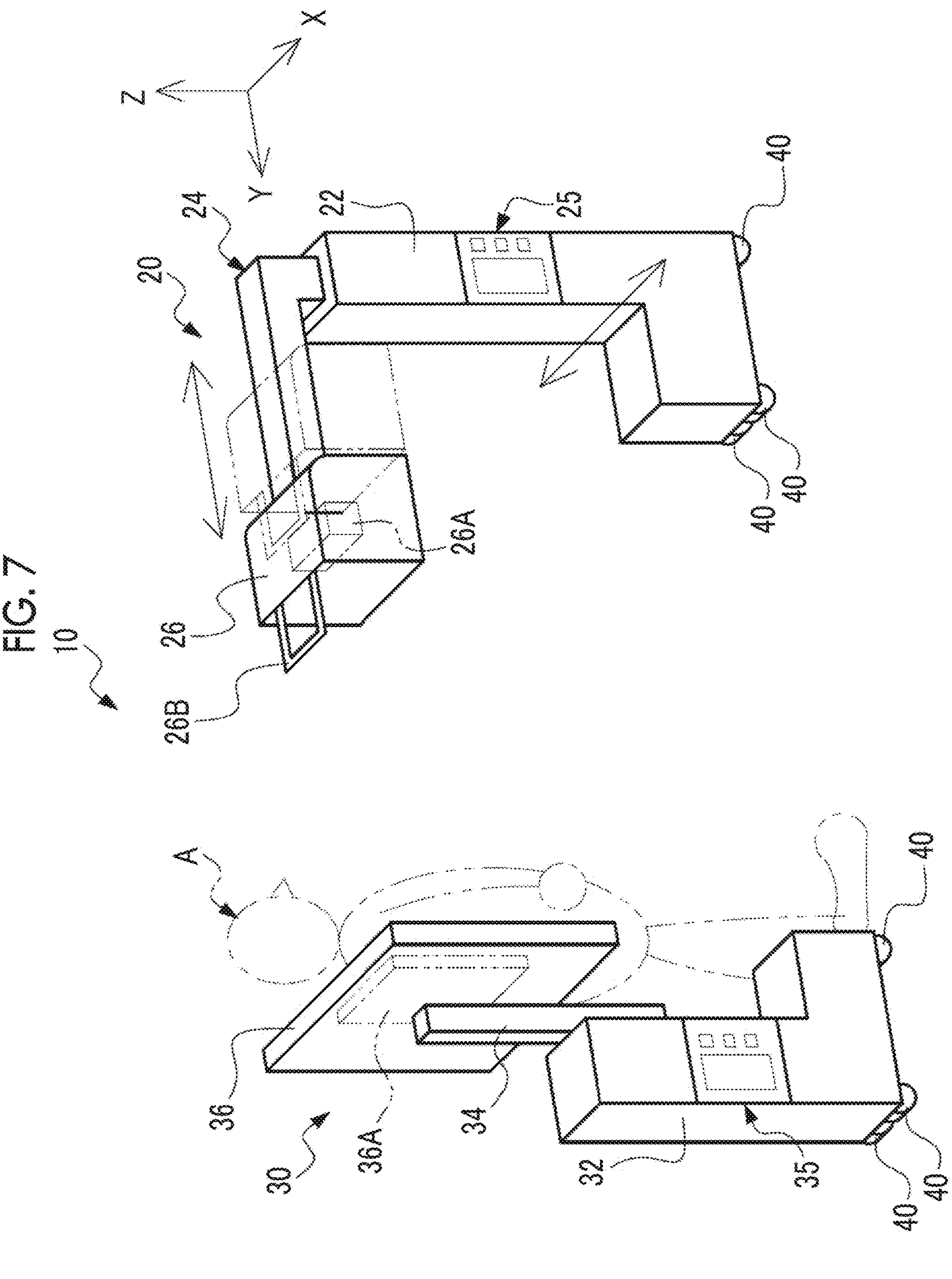
FIG. 7 is a schematic perspective view showing an example of a configuration of the radiography system according to the embodiment.

As illustrated in FIG. 7 as an example, the arm 24 is capable of being displaced in order to move the radiation emitting unit 26 relative to the subject A. The arm 24 is expandable and contractible in the horizontal direction. This allows the radiation emitting unit 26 to be moved relative to the subject A via the arm 24. In the example shown in FIG. 7, the arm 24 is expandable and contractible in the front-rear direction of the radiation source unit 20 (the direction along the Y direction shown in FIG. 7).

In the radiation source unit 20, the arm 24 is capable of moving the radiation emitting unit 26 in a direction (here, the front-rear direction) intersecting the movable direction the radiation source unit 20. More specifically, since the rotation of the main wheels 42A and 42B of the wheel portion 40 of the radiation source unit 20 is restricted by the brake mechanism 46, the movement direction of the radiation source unit 20 is only in the left-right direction. Here, after the position in the left-right direction has been manually adjusted, it is necessary to adjust the position of the radiation emitting unit 26 in the front-rear direction. In this case, in the radiation source unit 20 according to the present embodiment, the arm 24 is expanded and contracted in the front-rear direction to adjust the position of the radiation emitting unit 26 in the front-rear direction. Of course, after the position adjustment by the arm 24, the radiation source unit 20 may be moved.

Figure 8:
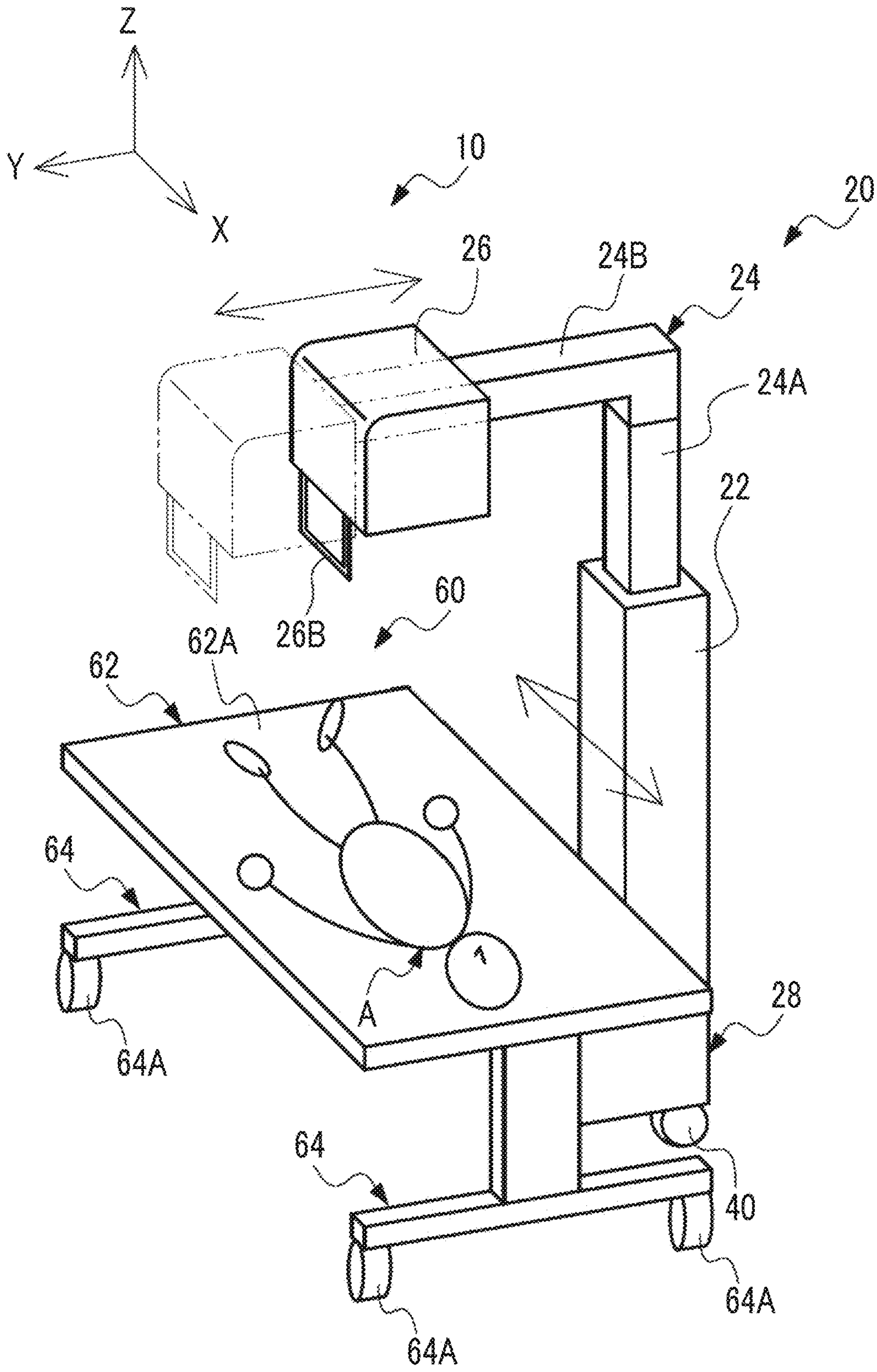
FIG. 8 is a schematic perspective view showing an example of a configuration of the radiography system according to the embodiment.

As an example, as shown in FIG. 8, in the radiography system 10 according to the present embodiment, the radiation source unit 20 may be used together with a decubitus table 60. In this case, the radiography system 10 includes a radiation source unit 20 and a decubitus table 60. The decubitus table 60 is a table on which the subject A can be placed. In a state in which the subject A is placed on the decubitus table 60, the subject A is irradiated with radiation, and radiography is performed. In the example shown in FIG. 8, the radiation emitting unit 26 emits radiation downward.

The decubitus table 60 comprises a placement part 62 and a leg part 64. The placement part 62 is a flat plate-shaped part on which the subject A is placed. In the example shown in FIG. 8, the placement part 62 has a rectangular parallelepiped shape with the longitudinal direction being the front-rear direction. The placement part 62 has a placement surface 62A on the upper side on which the subject A is placed. That is, the placement surface 62A has a rectangular parallelepiped shape in a plan view. The decubitus table 60 is, for example, a bed dedicated to radiography. The decubitus table 60 is provided with a radiation detector (not shown).

In addition, a leg part 64 is provided on the lower surface of the placement part 62. The leg part 64 is a member that supports the placement part 62. The leg part 64 set the placement part 62 at a predetermined height from the floor surface. In the example shown in FIG. 8, the leg parts 64 are provided on both ends of the placement part 62 in the front-rear direction, respectively. Each of the pair of leg parts 64 is provided with a wheel 64A. In the example shown in FIG. 8, the wheels 64A are provided at both end parts of the leg part 64 in the left-right direction one by one. The decubitus table 60 is movable by the wheels 64A. The decubitus table 60 may not have wheels 64A and may be fixed to the floor surface.

The arm 24 is expandable and contractible in the up-down direction. The arm 24 is also expandable and contractible in the horizontal direction. In the example shown in FIG. 8, the arm 24 is expandable and contractible in the front-rear direction of the radiation source unit 20 (the direction along the Y direction shown in FIG. 8). Specifically, a horizontal portion 24B of the arm 24 is expandable and contractible in the front-rear direction relative to a vertical portion 24A.

Accordingly, in the radiation source unit 20, the arm 24 is capable of moving the radiation emitting unit 26 in a direction (here, the front-rear direction) orthogonal to the movable direction the radiation source unit 20. In the radiation source unit 20 according to the present embodiment, the arm 24 is expanded and contracted in the front-rear direction to adjust the position of the radiation emitting unit 26 in the front-rear direction.

As described above, in the radiation source unit 20 according to the present embodiment, the wheel portions 40A to 40D are disposed in such a manner that the directions of movement caused by the rotation of the main wheels 42A and 42B are the same. Accordingly, the radiation source unit 20 can be moved while being supported by the plurality of wheel portions 40 in the movement direction of the radiation source unit 20, thereby stabilizing manual movement. In addition, movement is possible due to the rotation of the auxiliary wheels 44A and 44B in a direction orthogonal to the direction of movement caused by the rotation of the main wheels 42A and 42B. Accordingly, while the brake mechanism 46 restricts movement due to the rotation of the wheel portions 40A to 40D, movement is possible due to the rotation of the auxiliary wheels 44A and 44B. As a result, the movement direction of the radiation source unit 20 is limited to one direction only, making it easy to manually adjust the position.

Further, in the radiation source unit 20 according to the present embodiment, the arm 24 that supports the radiation emitting unit 26 is provided. The arm 24 is capable of moving the radiation emitting unit 26 in a direction (for example, the front-rear direction) intersecting the movement direction (for example, the left-right direction) of the radiation source unit 20. Specifically, the arm 24 is capable of expanding and contracting in the front-rear direction. This allows the position of the radiation emitting unit 26 to be adjusted in a direction in which the radiation source unit 20 cannot move.

Second Modification Example

In the above first embodiment, an example of a form in which the four wheel portions 40A to 40D are provided has been described, but the technology of the present disclosure is not limited thereto. The number and disposition of the wheel portions 40 are not particularly limited. As an example, as shown in <A> of FIG. 9, two wheel portions 40 and a ball caster 50 may be provided on the base portion 28. In this case, the two wheel portions 40 are disposed in such a manner that the directions of movement caused by the rotation of the main wheels 42A and 42B are the same. In addition, the two wheel portions 40 and the ball caster 50 are disposed at positions of the vertices of an imaginary triangle formed within the frame of the base portion 28 in a case in which the base portion 28 is viewed from below.

Figure 9:
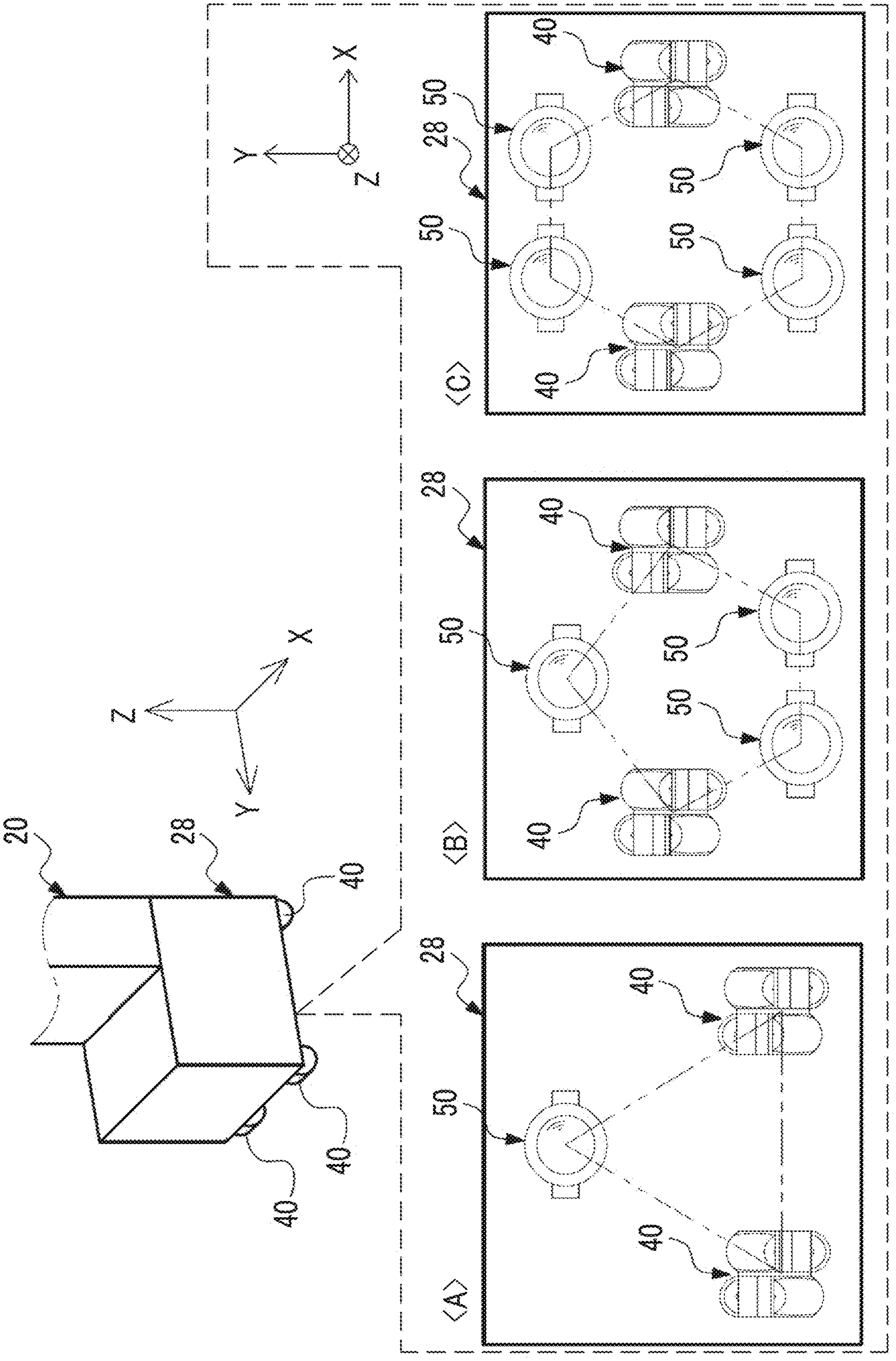
FIG. 9 is a conceptual diagram showing an example of a configuration of the radiation source unit according to the embodiment.

Also, as shown in <B> of FIG. 9 as an example, the two wheel portions 40 and three ball casters 50 may be provided on the base portion 28. In this case, the two wheel portions 40 are disposed in such a manner that the directions of movement caused by the rotation of the main wheels 42A and 42B are the same. The two wheel portions 40 and the three ball casters 50 are disposed at positions of the vertices of an imaginary pentagon formed within the frame of the base portion 28 in a case in which the base portion 28 is viewed from below. The disposition of the wheel portions 40 and the ball casters 50 is not particularly limited.

Also, as shown in <C> of FIG. 9 as an example, the two wheel portions 40 and four ball casters 50 may be provided on the base portion 28. The two wheel portions 40 and the four ball casters 50 are disposed at positions of the vertices of an imaginary hexagon formed within the frame of the base portion 28 in a case in which the base portion 28 is viewed from below. The disposition of the wheel portions 40 and the ball casters 50 is not particularly limited.

Third Embodiment

In the above first embodiment, an example of a form in which omni-wheels are used as the main wheels 42A and 42B in the wheel portion 40 has been described, but the technology of the present disclosure is not limited thereto. In this third embodiment, a Mecanum wheel is used as a main wheel 72 in a wheel portion 70.

Figure 10:
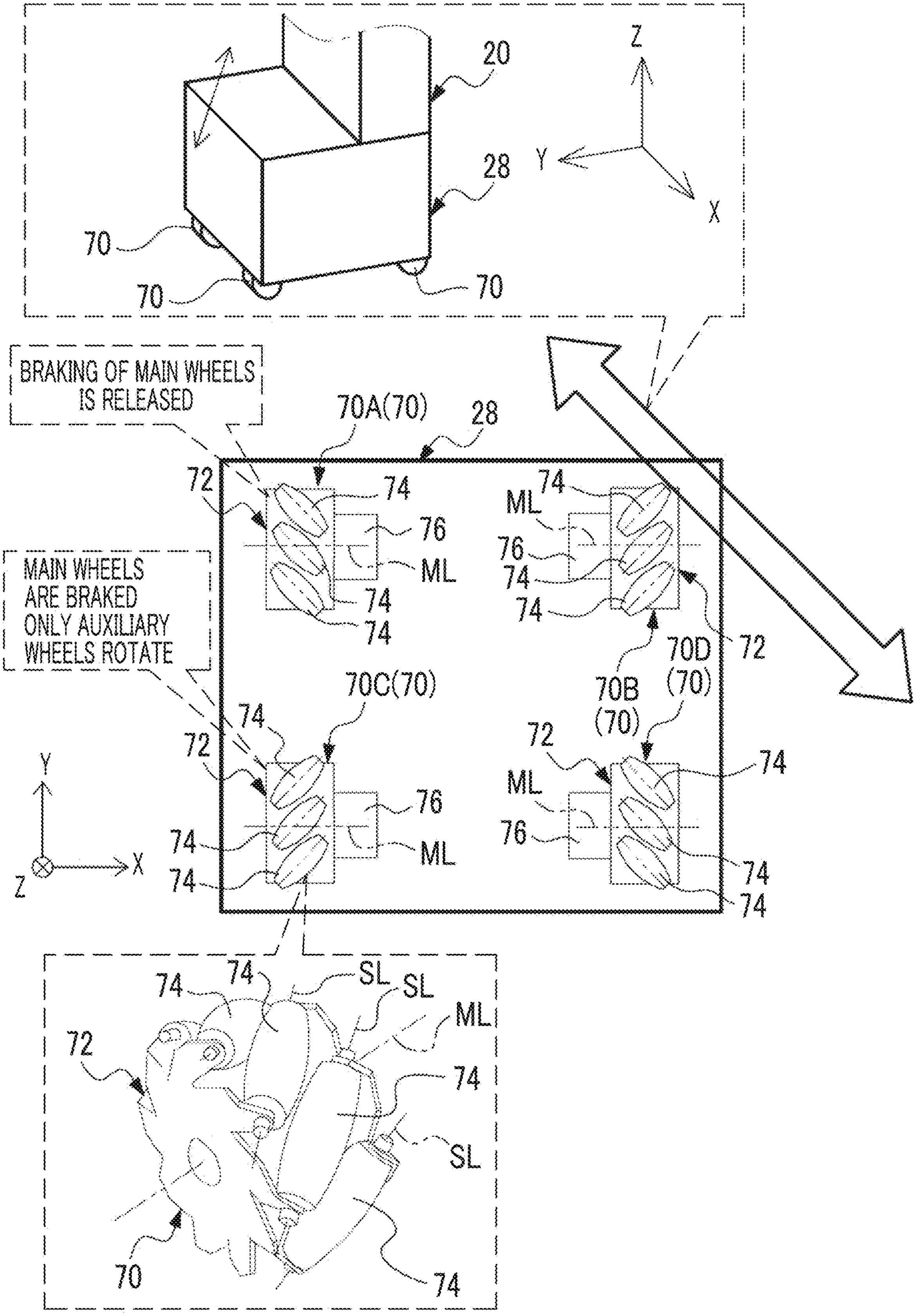
FIG. 10 is a conceptual diagram showing an example of a configuration of the radiation source unit according to the embodiment.

As an example, as shown in FIG. 10, the base portion 28 is provided with a wheel portion 70. In the example shown in FIG. 10, a plurality of wheel portions 70 are provided. Specifically, four wheel portions 70A to 70D are provided. The base portion 28 has a quadrangular outer frame as viewed from below, and wheel portions 70A to 70D are provided at the four corners of the quadrangle, respectively. That is, a wheel portion 70A is provided at the right front corner of the quadrangular base portion 28, and a wheel portion 70B is provided at the left front corner. In addition, a wheel portion 70C is provided at the right rear corner, and a wheel portion 70D is provided at the left rear corner. Hereinafter, in a case in which there is no need to distinguish between the wheel portions 70A to 70D, they will be simply referred to as a "wheel portion 70".

The wheel portion 70 has main wheels 72. The main wheels 72 are wheels for enabling the radiation source unit 20 to travel. The main wheel 72 is rotatable about a rotation axis ML. Except in the case in which the position is adjusted manually, the main wheels 72 may be rotatable by receiving power from a power source (not shown).

The wheel portion 70 has auxiliary wheels 74 arranged circumferentially in the rotation direction of the main wheels 72. Specifically, the main wheel 72 includes auxiliary wheels 74, and the auxiliary wheels 74 are attached along the outer periphery of the main wheels 72. In other words, the auxiliary wheels 74 form the outer peripheral surface of the main wheels 72 that can come into contact with the ground. The auxiliary wheel 74 has a spindle shape and is rotatable about a rotation axis SL that is aligned with the central axis of the spindle shape. The rotation axis SL of the auxiliary wheel 74 is inclined at a predetermined angle (for example, 45°) with respect to the rotation axis ML of the main wheel 72. In other words, the direction of movement caused by the rotation of the auxiliary wheels 74 is inclined with respect to the direction of movement caused by the rotation of the main wheel 72. In the example shown in FIG. 10, ten auxiliary wheels 74 are provided.

The auxiliary wheels 74 are formed of a material having a friction coefficient capable of suppressing movement due to rotation of the main wheels 72 in a state in which the rotation of the main wheels 72 is restricted by a brake mechanism 76. The auxiliary wheels 74 are formed of, for example, a synthetic resin material.

The main wheels 72 are, for example, so-called Mecanum Wheels (registered trademark). Although an example of a Mecanum wheel having ten auxiliary wheels 74 is given here, this is merely one example. For example, there may be less than ten or eleven or more auxiliary wheels 74.

In the wheel portions 70A and 70D, the inclination direction of the rotation axis SL of the auxiliary wheel 74 relative to the rotation axis ML of the main wheel 72 is the same. In addition, the wheel portions 70B and 70C, the inclination direction of the rotation axis SL of the auxiliary wheel 74 relative to the rotation axis ML of the main wheel 72 is the same. Furthermore, the inclination direction of the auxiliary wheels 74 in the wheel portions 70A and 70D is opposite to the inclination direction of the auxiliary wheels 74 in the wheel portions 70B and 70C.

The brake mechanism 76 is provided on the base portion 28. The brake mechanism 76 is a mechanism capable of restricting the rotation of the main wheels 72 of the wheel portion 70. The brake mechanism 76 is not particularly limited, and a general wheel braking mechanism may be employed. In the example shown in FIG. 10, the brake mechanism 76 is provided for each of the plurality of wheel portions 70.

In a state of not being braked by the brake mechanism 76, the radiation source unit 20 is movable in the front-rear direction and the left-right direction by the plurality of wheel portions 70. For example, in a case in which the radiation source unit 20 is moved manually by a user, the radiation source unit 20 is movable in the front-rear direction by a plurality of wheel portions 70. Further, for example, by receiving power from a power source (not shown), the main wheels 72 of all the wheel portions 70A to 70D rotate in the same rotation direction, thereby achieving movement in the front-rear direction. In addition, the main wheels 72 in the wheel portions 70A and 70D rotate in the same rotation direction as each other, and the main wheels 72 in the wheel portions 70B and 70C rotate in the same rotation direction as each other but in the opposite direction to the rotation direction of the wheel portions 70A and 70D, thereby achieving the movement in the left-right direction.

In response to an operation on the operation unit 25, the brake mechanism 76 restricts the rotation of the main wheels 72. The operation unit 25 can receive an operation of setting the movable direction of the radiation source unit 20 to either a left oblique direction or a right oblique direction. In the case of movement in a left oblique direction, the rotation of the main wheels 72 in the wheel portions 70B and 70C is restricted by the brake mechanism 76. On the other hand, the restriction by the brake mechanism 76 is released for the wheel portions 70A and 70D.

In addition, in the case of movement in a right oblique direction, the rotation of the main wheels 72 of the wheel portions 70A and 70D is restricted by the brake mechanisms 76. On the other hand, the restriction by the brake mechanism 76 is released for the wheel portions 70B and 70C.

After the state of restriction of the wheel portion 70 by the brake mechanism 76 is changed in response to an operation on the operation unit 25, the user manually moves the radiation source unit 20 only in a predetermined direction to adjust the position. In the example shown in FIG. 10, the radiation source unit 20 is moved in a left oblique direction (that is, a direction inclined to the left side with respect to the front-rear direction) by rotation of the main wheels 72 and the auxiliary wheels 74 of each of the wheel portions 70A and 70D. On the other hand, in the wheel portions 70B and 70C, the rotation of the main wheels 72 is restricted by the brake mechanism 76. In this case, the wheel portions 70B and 70C achieve movement in the left oblique direction by rotation of the auxiliary wheels 74. In this manner, in the wheel portions 70B and 70C in which the rotation of the main wheels 72 is restricted by the brake mechanism 76, movement in the left oblique direction is achieved by the rotation of the auxiliary wheels 74. The user adjusts the position of the radiation source unit 20 in the left oblique direction.

The auxiliary wheels 74 are formed of a material (for example, a synthetic resin material such as rubber) having a friction coefficient capable of restricting movement in a right oblique direction. That is, in the wheel portions 70B and 70C, the movement in the right oblique direction is also restricted by the contact of the auxiliary wheels 74 with the floor surface.

As described above, in the radiation source unit 20 according to the third embodiment, the direction of movement caused by the rotation of the auxiliary wheels 74 is the inclined direction (for example, the left oblique direction) with respect to the direction of movement caused by the rotation of the main wheels 72 (for example, the front-rear direction). Accordingly, the movable direction of the radiation source unit 20 is limited to only one direction (only the left oblique direction in this case), making it easy to manually adjust the position of the radiation source unit 20.

Fourth Embodiment

In the above first embodiment, an example of a form in which the operation unit 25 is provided on the body part 22 of the radiation source unit 20 has been described, but the technology of the present disclosure is not limited thereto. In this fourth embodiment, an operation unit 27 is provided in the radiation emitting unit 26.

Figure 11:
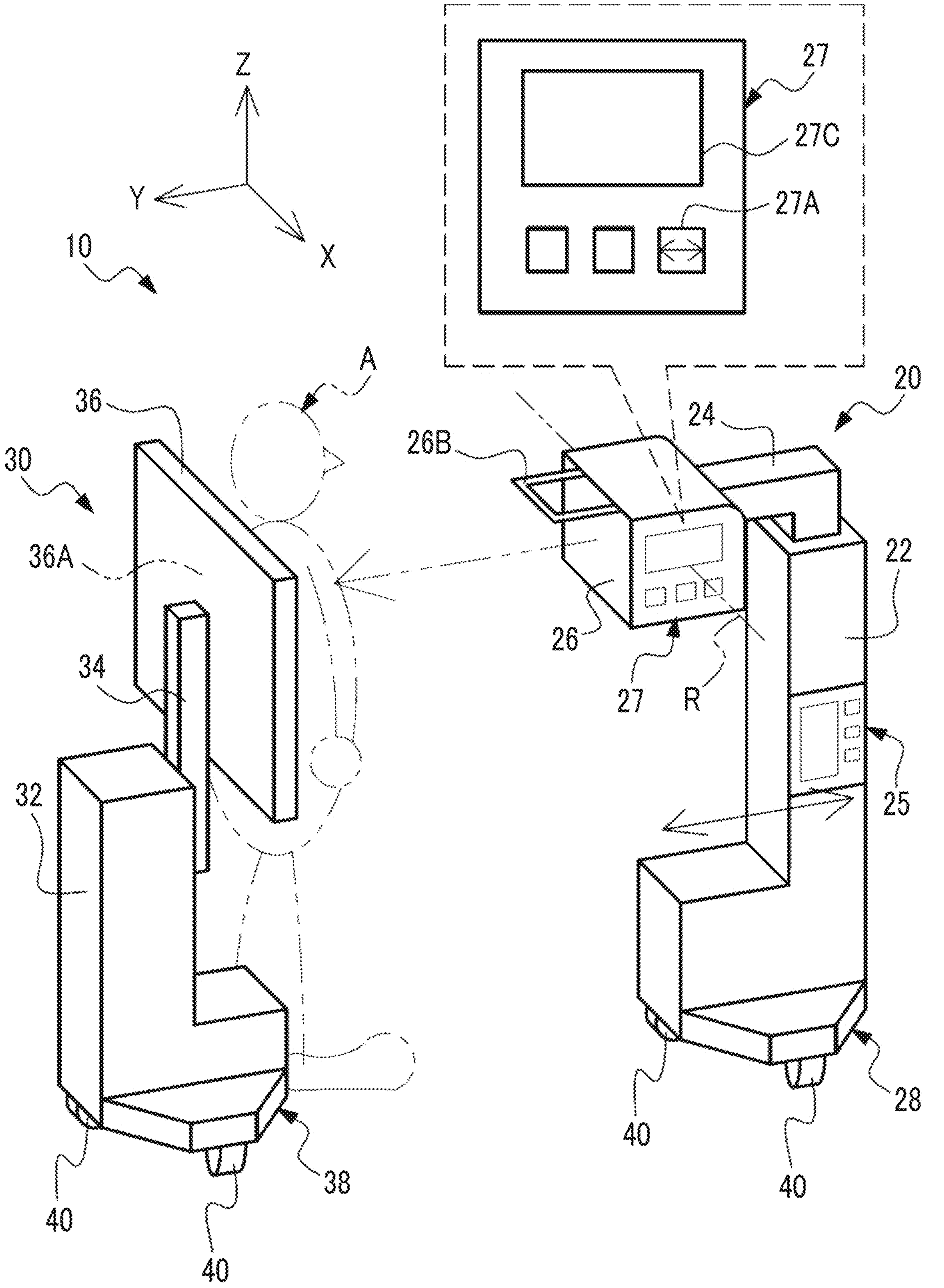
FIG. 11 is a schematic perspective view showing an example of a configuration of the radiography system according to the embodiment.

As an example, as shown in FIG. 11, the radiation emitting unit 26 is provided with an operation unit 27. The operation unit 27 has a similar configuration to the operation unit 25 provided on the body part 22. The operation unit 27 is capable of receiving an operation of setting the direction of movement of the radiation source unit 20 by the wheel portion 40 to a predetermined direction. Specifically, the operation unit 25 can receive an operation of setting the movable direction of the radiation source unit 20 to either the left-right direction or the front-rear direction. In the example shown in FIG. 11, the operation unit 25 is an operation panel provided on the left side surface of the radiation emitting unit 26.

The operation unit 27 is provided with a forward/backward movement button 27A. The forward/backward movement button 27A receives an operation of setting the movement direction of the radiation source unit 20 to the front-rear direction (the direction along the Y direction shown in FIG. 11). By pressing the forward/backward movement button 27A, the state in which the brake mechanism 46 restricts the wheel portion 40 is changed, and the movement direction of the wheel portion 40 is limited to the front-rear direction.

Figure 12:
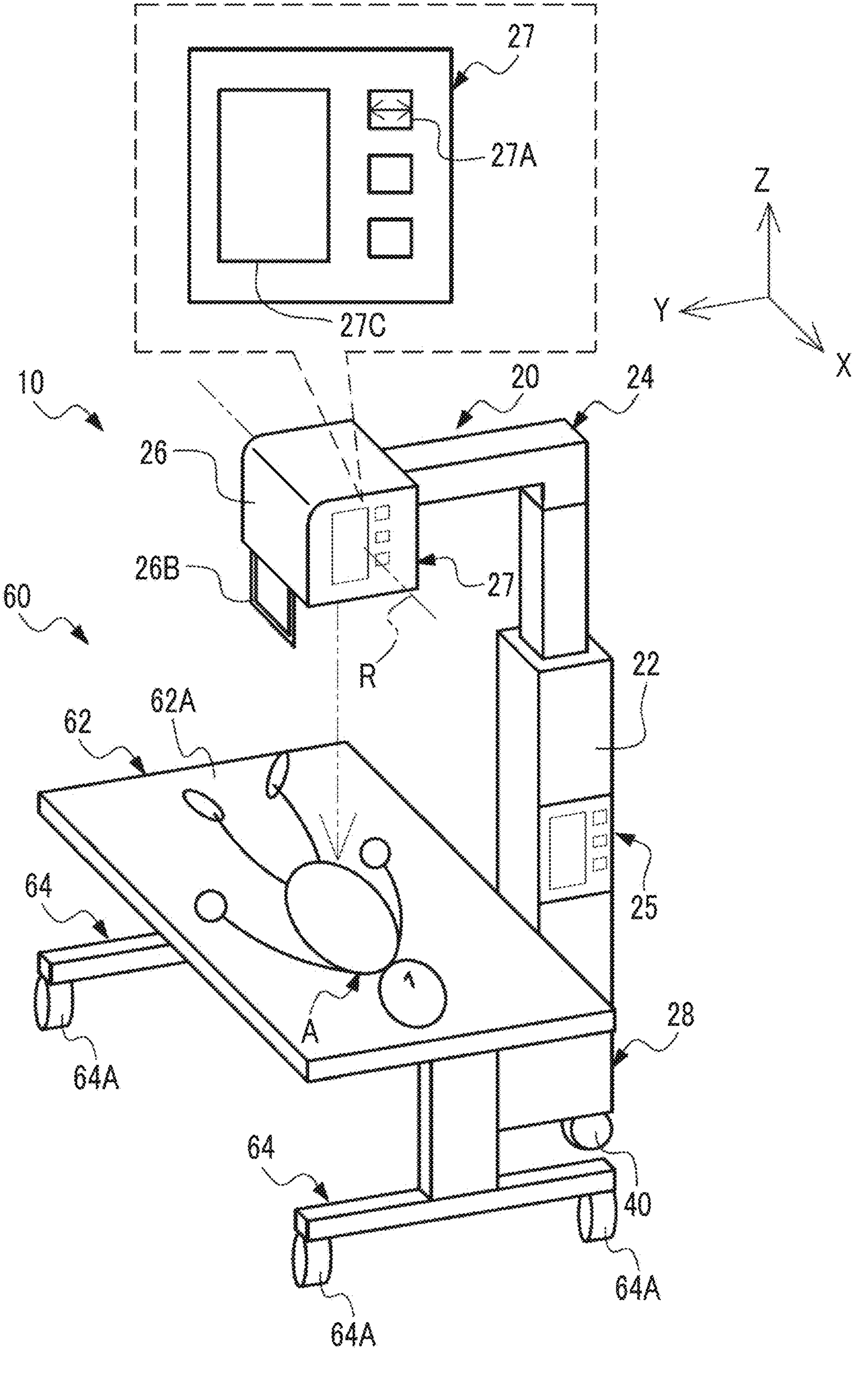
FIG. 12 is a schematic perspective view showing an example of a configuration of the radiography system according to the embodiment.

In the case of upright imaging performed on a subject A in a standing state as shown in FIG. 11, the irradiation direction of the radiation is a horizontal direction. Therefore, the radiation emitting unit 26 is set in an orientation such that the irradiation direction of the radiation is horizontal. On the other hand, as shown in FIG. 12, in a case in which the radiation source unit 20 is used together with the decubitus table 60 (that is, in the case of decubitus imaging), the irradiation direction of the radiation is in the up-down direction. Therefore, the radiation emitting unit 26 is set in an orientation such that the irradiation direction of the radiation is downward. Since it is necessary to switch the irradiation direction of the radiation by 90° between upright imaging and decubitus imaging in this manner, the radiation emitting unit 26 is rotated by 90° about a rotation axis R that is an axis extending in the left-right direction.

The forward/backward movement button 27A provided on the operation unit 27 can indicate the movable direction of the radiation source unit 20. Specifically, the forward/backward movement button 27A is a button equipped with a liquid crystal display function. The forward/backward movement button 27A displays the movable direction of the radiation source unit 20 with a double-headed arrow. In the example shown in FIG. 11, a double-headed arrow along the left-right direction as viewed from the front side of the page is displayed on the liquid crystal screen of the forward/backward movement button 27A. The forward/backward movement button 27A is an example of a "display unit" according to the technology of the present disclosure.

As described above, the radiation emitting unit 26 rotates in accordance with the change in imaging method. Therefore, the operation unit 25 also rotates in accordance with the rotational movement. For example, in a case in which the operation unit 25 is provided on a side surface (here, the left side surface of the radiation emitting unit 26) whose normal direction is along the rotation axis R, as the operation unit 25 rotates, the movable direction displayed on the operation unit 25 (for example, a double-headed arrow indicating the movement direction) also rotates. In this case, in a case in which the display of the movable direction remains the same after rotation, the user may erroneously recognize the movable direction depending on the displayed movement direction. For example, the double-headed arrow displayed on the forward/backward movement button 27A shown in FIG. 11 is rotated counterclockwise as viewed from the front side of the page. Accordingly, the double-headed arrow along the left-right direction becomes a double-headed arrow along the up-down direction. For this reason, the user erroneously recognizes the forward/backward movement button 27A as a button that receives an operation for moving in the up-down direction.

Therefore, the display on the forward/backward movement button 27A is switched depending on the irradiation direction of the radiation by the radiation emitting unit 26. For example, the irradiation direction of the radiation is detected by an angle sensor provided in the radiation emitting unit 26, and the display on the operation unit 25 is switched based on a result of the detection. In the example shown in FIG. 12, a double-headed arrow along the left-right direction as viewed from the front side of the page is displayed on the liquid crystal screen of the forward/backward movement button 27A. That is, even after the radiation emitting unit 26 is rotated, the movement direction displayed by the forward/backward movement button 27A remains consistent with the movable direction of the radiation source unit 20. In this way, the display on the forward/backward movement button 27A is switched depending on the irradiation direction of the radiation by the radiation emitting unit 26. Then, the user recognizes the display content of the forward/backward movement button 27A and presses the forward/backward movement button 27A. Furthermore, the user manually adjusts the position of the radiation source unit 20 in the front-rear direction.

As described above, in the radiation source unit 20 according to the present embodiment, the operation unit 27 is provided in the radiation emitting unit 26. Accordingly, in a case of manually adjusting the position of the radiation source unit 20 while gripping a part of the radiation emitting unit 26 (for example, the grip portion 26B), the gripping position and the position of the operation unit 27 are close to each other, making it easier to operate the operation unit 27.

In addition, in the radiation source unit 20 according to the present embodiment, the operation unit 27 has a forward/backward movement button 27A that indicates the movable direction of the radiation source unit 20. The display of the movement direction on the forward/backward movement button 27A is switched depending on the irradiation direction of the radiation by the radiation emitting unit 26. This makes it easy to know the direction in which the radiation source unit 20 can be manually moved, even in a case in which the irradiation direction of the radiation is changed depending on the radiography method.

In the above fourth embodiment, an example of a form in which the forward/backward movement button 27A is a button with a liquid crystal display function has been described, but the technology of the present disclosure is not limited thereto. For example, in the case in which the operation unit 27 is a touch panel, the display of a soft button representing the forward/backward movement button 27A may be switched depending on the irradiation direction of radiation.

Further, in each of the above embodiments, an example of a form in which the decubitus table 60 is a dedicated bed for radiography has been described, but the technology of the present disclosure is not limited thereto. The decubitus table 60 may be a bed provided in a general hospital ward or a general examination table.

The described contents and illustrated contents shown above are detailed descriptions of the parts related to the technology of the present disclosure, and are merely an example of the technology of the present disclosure. For example, the above description of the configuration, function, operation, and effect is an example of the configuration, function, operation, and effect of the parts related to the technology of the present disclosure. Therefore, needless to say, unnecessary parts may be deleted, new elements may be added, or replacements may be made to the described contents and illustrated contents shown above within a range that does not deviate from the gist of the technology of the present disclosure. Further, in order to avoid complications and facilitate understanding of the parts related to the technology of the present disclosure, descriptions of common general knowledge and the like that do not require special descriptions for enabling the implementation of the technology of the present disclosure are omitted, in the described contents and illustrated contents shown above.

In the present specification, the term "A and/or B" is synonymous with the term "at least one of A or B". That is, the term "A and/or B" means that only A may be used, only B may be used, or a combination of A and B may be used. In addition, in the present specification, the same approach as "A and/or B" is applied to a case in which three or more matters are represented by connecting the matters with "and/or".

All documents, patent applications, and technical standards described in the present specification are incorporated in the present specification by reference to the same extent as in a case in which each of the documents, patent applications, and technical standards are specifically and individually indicated to be incorporated by reference.

Regarding the embodiments, the following supplementary notes are further disclosed.

Supplementary Note 1

A radiography unit comprising:

a wheel portion including a first wheel provided at a lower portion of a unit and movable in a first direction by rotation, and a second wheel arranged circumferentially in a rotation direction of the first wheel and movable in a second direction different from the first direction by rotation;

a brake mechanism configured to restrict the rotation of the first wheel; and an operation unit configured to receive an operation of changing a state of restriction of the wheel portion by the brake mechanism, the operation being to set a movement direction of the unit by the wheel portion to one direction, in which, in a case in which the rotation of the first wheel is restricted by the brake mechanism in response to an operation on the operation unit and movement in another direction intersecting the one direction is restricted, movement in the one direction is enabled by the rotation of the second wheel.

Supplementary Note 2

The radiography unit according to Supplementary Note 1, in which a plurality of the wheel portions are provided, and the plurality of wheel portions include a first wheel portion which is the wheel portion disposed in an orientation in which the first direction is the one direction, and a second wheel portion which is the wheel portion disposed in an orientation in which the first direction is the other direction.

Supplementary Note 3

The radiography unit according to Supplementary Note 2, in which the operation unit is configured to receive an operation of setting a movable direction of the radiography unit to either the one direction or the other direction, and in response to the operation on the operation unit, the restriction of the rotation of the first wheel by the brake mechanism in the first wheel portion and the restriction of the rotation of the first wheel by the brake mechanism in the second wheel portion are selectively switched, thereby switching the movable direction to the one direction or the other direction.

Supplementary Note 4

The radiography unit according to Supplementary Note 2 or 3, in which the number of the first wheel portions and the number of the second wheel portions are the same.

Supplementary Note 5

The radiography unit according to any one of Supplementary Notes 2 to 4, in which the plurality of wheel portions include two or more of the first wheel portions and two or more of the second wheel portions.

Supplementary Note 6

The radiography unit according to Supplementary Note 1, in which a plurality of the wheel portions are provided, and the plurality of wheel portions are disposed in such a manner that the first direction is the same.

Supplementary Note 7

The radiography unit according to Supplementary Note 6, in which the radiography unit is a radiation source unit including a radiation emitting unit configured to emit radiation and an arm that supports the radiation emitting unit, and the arm is configured to move the radiation emitting unit in a direction intersecting a movement direction of the radiography unit.

Supplementary Note 8

The radiography unit according to any one of Supplementary Notes 1 to 7, in which, in the wheel portion, the second direction is a direction orthogonal to the first direction.

Supplementary Note 9

The radiography unit according to Supplementary Note 8, in which the second wheel is formed of a material having a friction coefficient configured to suppress the movement in the other direction in the wheel portion in which the rotation of the first wheel is restricted by the brake mechanism.

Supplementary Note 10

The radiography unit according to any one of Supplementary Notes 1 to 7, in which, in the wheel portion, the second direction is a direction inclined with respect to the first direction.

Supplementary Note 11

The radiography unit according to Supplementary Note 1, in which the radiography unit is a radiation source unit including a radiation emitting unit configured to emit radiation, and the operation unit is provided in the radiation emitting unit.

Supplementary Note 12

The radiography unit according to Supplementary Note 11, in which the operation unit has a display unit that indicates a movable direction of the radiation source unit, and a display on the display unit is switched depending on an irradiation direction of the radiation by the radiation emitting unit.

Supplementary Note 13

A radiography system comprising:

a radiation source unit that includes a radiation emitting unit configured to emit radiation; and a detection unit that includes a radiation detection unit configured to detect the radiation, in which the radiation source unit and/or the detection unit is the radiography unit according to any one of Supplementary Notes 1 to 6.

EXPLANATION OF REFERENCES

What is claimed is:

1. A radiography unit comprising:

a base portion provided at a lower portion of a unit;

a plurality of wheel portions provided on the base portion, each of the plurality of wheel portions including a first wheel movable in a first direction by rotation, and a second wheel arranged circumferentially in a rotation direction of the first wheel and movable in a second direction different from the first direction by rotation;

a brake mechanism configured to restrict the rotation of the first wheel; and an operation unit configured to receive an operation of changing a state of restriction of the wheel portion by the brake mechanism, the operation being to set a movement direction of the unit by the wheel portion to one direction, wherein, in a case in which the rotation of the first wheel is restricted by the brake mechanism in response to the operation on the operation unit and movement in another direction intersecting the one direction is restricted, movement in the one direction is enabled by the rotation of the second wheel, wherein at least one of the plurality of wheel portions is provided at each of both end portions in a front-rear direction of the base portion, at each of both end portions in a left-right direction of the base portion, or at each of both end portions in a front-rear direction of the base portion and at each of both end portions in a left-right direction of the base portion.

2. The radiography unit according to claim 1, wherein a plurality of the wheel portions are provided, and the plurality of wheel portions include a first wheel portion which is the wheel portion disposed in an orientation in which the first direction is the one direction, and a second wheel portion which is the wheel portion disposed in an orientation in which the first direction is the other direction.

3. The radiography unit according to claim 2, wherein the operation unit is configured to receive an operation of setting a movable direction of the radiography unit to either the one direction or the other direction, and in response to the operation on the operation unit, the restriction of the rotation of the first wheel by the brake mechanism in the first wheel portion and the restriction of the rotation of the first wheel by the brake mechanism in the second wheel portion are selectively switched, thereby switching the movable direction to the one direction or the other direction.

4. The radiography unit according to claim 2, wherein the number of the first wheel portions and the number of the second wheel portions are the same.

5. The radiography unit according to claim 2, wherein the plurality of wheel portions include two or more of the first wheel portions and two or more of the second wheel portions.

6. The radiography unit according to claim 1, wherein a plurality of the wheel portions are provided, and the plurality of wheel portions are disposed in such a manner that the first direction is the same.

7. The radiography unit according to claim 6,
wherein the radiography unit is a radiation source unit including a radiation emitting unit configured to emit radiation and an arm that supports the radiation emitting unit, and
the arm is configured to move the radiation emitting unit in a direction intersecting a movement direction of the radiography unit.

8. The radiography unit according to claim 1,
wherein, in the wheel portion, the second direction is a direction orthogonal to the first direction.

9. The radiography unit according to claim 8,
wherein the second wheel is formed of a material having a friction coefficient configured to suppress the movement in the other direction in the wheel portion in which the rotation of the first wheel is restricted by the brake mechanism.

10. The radiography unit according to claim 1,
wherein, in the wheel portion, the second direction is a direction inclined with respect to the first direction.

11. The radiography unit according to claim 1,
wherein the radiography unit is a radiation source unit including a radiation emitting unit configured to emit radiation, and
the operation unit is provided in the radiation emitting unit.

12. The radiography unit according to claim 11,
wherein the operation unit has a display unit that indicates a movable direction of the radiation source unit, and
a display on the display unit is switched depending on an irradiation direction of the radiation by the radiation emitting unit.

13. A radiography system comprising:
a radiation source unit that includes a radiation emitting unit configured to emit radiation; and
a detection unit that includes a radiation detection unit configured to detect the radiation,
wherein the radiation source unit and/or the detection unit is the radiography unit according to claim 1.

* * * * *